(12) United States Patent
Kaji et al.

(10) Patent No.: US 6,865,896 B2
(45) Date of Patent: Mar. 15, 2005

(54) STORAGE UNIT AND REFRIGERATOR

(75) Inventors: Masaki Kaji, Sakai (JP); Yasuo Takenaka, Suita (JP); Hiroshi Yoshimura, Tondabayashi (JP)

(73) Assignee: Sharp Kabushiki Kaisha, Osaka (JP)

( * ) Notice: Subject to any disclaimer, the term of this patent is extended or adjusted under 35 U.S.C. 154(b) by 0 days.

(21) Appl. No.: 10/451,877

(22) PCT Filed: Dec. 25, 2001

(86) PCT No.: PCT/JP01/11403
§ 371 (c)(1),
(2), (4) Date: Jun. 26, 2003

(87) PCT Pub. No.: WO02/053993
PCT Pub. Date: Jul. 11, 2002

(65) Prior Publication Data
US 2004/0035128 A1 Feb. 26, 2004

(30) Foreign Application Priority Data

Dec. 27, 2000 (JP) .......................... 2000-397070
Jan. 31, 2001 (JP) .......................... 2001-022731
Mar. 7, 2001 (JP) .......................... 2001-062863
Apr. 4, 2001 (JP) .......................... 2001-105324

(51) Int. Cl.$^7$ .......................... F24F 3/16; F25D 23/00; B01J 19/08; B01J 19/12; G01T 1/18
(52) U.S. Cl. .......................... 62/78; 62/264; 422/186.04; 250/382
(58) Field of Search .......................... 62/264, 78, 331; 422/22, 29, 186.04; 250/382

(56) References Cited

U.S. PATENT DOCUMENTS

| 4,597,781 A | * | 7/1986 | Spector | 96/52 |
| 5,468,454 A | * | 11/1995 | Kim | 422/121 |
| 6,342,187 B1 | * | 1/2002 | Jacob et al. | 422/186.05 |
| 2003/0072675 A1 | * | 4/2003 | Takeda et al. | 422/22 |
| 2003/0137794 A1 | * | 7/2003 | Izumi et al. | 361/231 |
| 2004/0007000 A1 | * | 1/2004 | Takeda et al. | 62/78 |

FOREIGN PATENT DOCUMENTS

| JP | 05-149671 | * | 6/1993 |
| JP | 6-31099 U | | 4/1994 |
| JP | 7-280423 A | | 10/1995 |
| JP | 8-145545 A | | 6/1996 |
| JP | 11-47547 A | | 2/1999 |
| JP | 11-206529 A | | 8/1999 |
| JP | 2000-268938 A | | 9/2000 |
| JP | 2000-277235 A | | 10/2000 |

* cited by examiner

Primary Examiner—William C. Doerrler
(74) Attorney, Agent, or Firm—Birch, Stewart, Kolasch & Birch, LLP.

(57) ABSTRACT

The cool air inside a refrigerator compartment 2 is introduced through a return opening 10 into an ion generation chamber 45 provided behind the refrigerator compartment 2. A voltage is applied to a needle-like electrode 11a arranged in an upper portion of the ion generation chamber 45 so that, by corona discharge, positive and negative ions are discharged substantially parallel to the cool air circulating in the direction indicated by arrow B2. This helps alleviate the loss of ions resulting from collision with a wall surface, and permits the ions to reach a wide area. This prolongs the period for which the cool air is kept in contact with the ions, and thus helps enhance the sterilizing effect.

19 Claims, 23 Drawing Sheets

6,865,896 B2

STORAGE UNIT AND REFRIGERATOR

This application is the national phase under 35 U.S.C. § 371 of PCT International Application No. PCT/JP01/11403 which has an International filing date of Dec. 25, 2001, which designated the United States of America.

TECHNICAL FIELD

The present invention relates to a storeroom and a refrigerator provided with a sterilizing means for killing airborne bacteria floating in cool air inside a storage compartment.

BACKGROUND ART

A conventional refrigerator is disclosed in Japanese Patent Application Laid-Open No. H8-145545. According to this publication, inside a refrigerator is provided an ion generating device having an opposed electrode that attracts electric charge, and a negative direct-current high voltage is applied to the opposed electrode to produce negative ions. The negative ions are discharged into a storage compartment so as to restrain the proliferation of bacteria floating inside the storage compartment and thereby keep the food stored therein fresh.

In this conventional refrigerator, the ion generating device has an opposed electrode arranged so as to be opposed to a needle-like electrode. The ions discharged from the needle-like electrode into the narrow space between the needle-like and opposed electrodes are attracted by the opposed electrode. Thus, to discharge the desired number of ions required to kill bacteria into the storage compartment, it is necessary to use a large-size blower that has a high blowing ability. That is, one problem with this conventional structure is that the provision of the opposed electrode and the large-size blower tends to make the ion generating device complicated and large.

Moreover, when the needle-like electrode is charged with a negative voltage to selectively generate a large number of negative ions, the electric circuit is charged with positive electric charge. This causes failure of the electric circuit resulting from its being charged, and lowering of the number of generated negative ions under the influence of the positive electric charge. To avoid this, it is necessary to let the positive charge escape by securing direct grounding to the earth. Thus, another problem with the conventional structure is, in refrigerators for home use, it is difficult to secure direct grounding to the earth in all households because of restraints associated with the design, location, and the like of their homes.

DISCLOSURE OF THE INVENTION

An object of the present invention is to provide a storeroom and a refrigerator that can kill airborne bacteria efficiently. Another object of the present invention is to provide a storeroom and a refrigerator that do not require direct grounding to the earth and thus can be installed easily in a household and that do not require a complicated structure to bring ions into contact with airborne bacteria easily and thereby achieve an enhanced sterilizing effect.

To achieve the above objects, according to the present invention, in a storeroom or refrigerator, an electrode is provided to which a high voltage is applied to generate positive ions such as $H^+(H_2O)_n$ and negative ions such as $O_2^-(H_2O)_m$, and the positive and negative ions are discharged from the electrode into an air flow passage through which air is circulated in order to kill airborne germs floating in the air. The air flow passage includes a storage compartment and a duct provided behind the storage compartment.

According to the present invention, a high voltage is applied to an electrode to which no opposed electrode is provided to generate positive ions such as $H^+(H_2O)_n$ and negative ions such as $O_2^-(H_2O)_m$, and the positive and negative ions are discharged into an air flow passage through which air is circulated in order to kill airborne germs floating in the air.

According to the present invention, an ion generating device that does not require grounding is provided, and a high voltage is applied to an electrode of the ion generating device to generate positive ions such as $H^+(H_2O)_n$ and negative ions such as $O_2^-(H_2O)_m$. The positive and negative ions are discharged into an air flow passage through which air is circulated in order to kill airborne germs floating in the air.

According to the present invention, an ion generating device having no grounded electrode is provided, and a high voltage is applied to an electrode of the ion generating device to generate positive ions such as $H^+(H_2O)_n$ and negative ions such as $O_2^-(H_2O)_m$. The positive and negative ions are discharged into an air flow passage through which air is circulated in order to kill airborne germs floating in the air.

According to the present invention, one or more storage compartments are provided and the air flow passage includes at least one of the storage compartments so that the positive and negative ions are discharged into that storage compartment.

According to the present invention, radicals produced from the positive and negative ions kill airborne bacteria floating inside the air flow passage.

According to the present invention, one or more storage compartments are provided, at least one of the storage compartments is fitted with a duct through which air is introduced thereto, and the electrode is arranged in the duct.

According to the present invention, at least one storage compartment is provided, and controlling means for controlling the generation of the ions in synchronism with the circulation of air to that storage compartment is provided.

According to the present invention, at least one storage compartment is provided, cooling means for cooling the inside of that storage compartment is provided, and controlling means for controlling the generation of the ions in synchronism with the cooling of that storage compartment is provided.

According to the present invention, at least one storage compartment is provided, temperature detecting means is provided in that storage compartment, and controlling means for controlling the generation of the ions according to the result of temperature detection by the temperature detecting means is provided.

According to the present invention, controlling means for controlling the generation of the ions according to the result of detection of whether a damper for controlling a flow of air is open or closed is provided.

According to the present invention, at least one storage compartment is provided, cooling means for cooling the inside of that storage compartment is provided, and controlling means for controlling the generation of the ions in synchronism with the driving of a compressor constituting part of the cooling means is provided.

According to the present invention, at least one storage compartment is provided, and controlling means for controlling the generation of the ions in synchronism with the opening of at least one door for opening and closing that storage compartment or according to the result of detection of the opening movement of that door is provided.

According to the present invention, controlling means for controlling the generation of the ions according to the temperature outside is provided.

According to the present invention, at least one storage compartment is provided, cooling means for cooling the inside of that storage compartment is provided, temperature detecting means for detecting the temperature inside that storage compartment cooled by the cooling means is provided, and, when the temperature detected by the temperature detecting means becomes higher than a predetermined temperature, in synchronism with the cooling of the storage compartment, a voltage is applied to the ion generating device to generate the positive and negative ions.

BEST MODE FOR CARRYING OUT THE INVENTION

Figure 1:
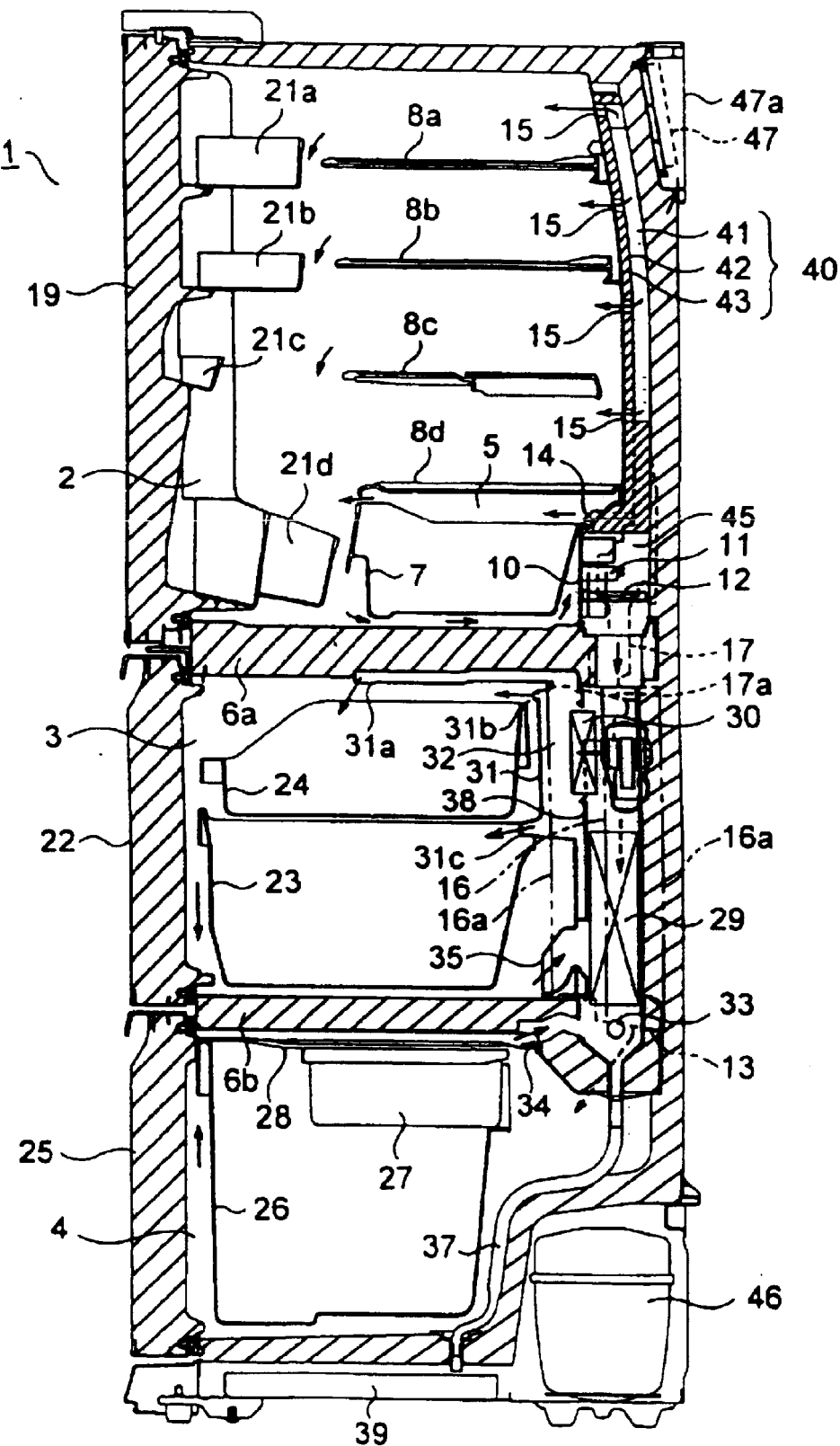
FIG. 1 is a side sectional view of the refrigerator of a first embodiment of the invention.

Hereinafter, embodiments of the present invention will be described with reference to the drawings. FIG. 1 is a side sectional view of the refrigerator of a first embodiment of the invention. The refrigerator has a refrigerator compartment 2, a freezer compartment 3, and a vegetables compartment 4 provided in this order from the top inside a main body 1 thereof, and these refrigerator, freezer, and vegetables compartments 2, 3, and 4 are separated from one another by partitions 6a and 6b. In a lower portion of the refrigerator compartment 2 is provided an isolated compartment 5, where a case 7 is housed that is movable back and forth. Moreover, in the refrigerator compartment 2 are provided shelves 8a to 8d to put food and the like on, with the shelf 8d forming the ceiling of the isolated compartment 5.

The refrigerator compartment 2 is opened and closed with a refrigerator compartment door 19 pivotably supported on the front face of the refrigerator compartment 2. In the rear surface of the refrigerator compartment door 19 are provided door pockets 21a to 21d. The freezer compartment 3 is opened and closed with a drawer-type freezer compartment door 22. A freezer case 23 is detachably fitted to the freezer compartment door 22 so that it can be pulled out together with the freezer compartment door 22. Another freezer case 24 is arranged above the freezer case 23 so that it can be pulled out separately from the freezer compartment door 22.

The vegetables compartment 4 is opened and closed with a drawer-type vegetables compartment door 25. A vegetables case 26 is fitted to the vegetables compartment door 25 so that it can be pulled out together with the vegetables compartment door 25. In an upper portion of the vegetables case 26 is arranged a small articles case 27. The top face of the vegetables case 26 is covered with a vegetables case cover 28 so that a predetermined humidity is maintained inside the vegetables case 26 and the small articles case 27.

Behind the freezer compartment 3, a cool air passage 38 is provided, and inside the cool air passage 38 is arranged a chiller 29 that produces cool air as a compressor 46 is driven. Below the chiller 29 is arranged a heater 33 for defrosting the chiller 29. The water produced as a result of the defrosting by the heater 33 is collected through a drain pipe 37 in a vaporizing pan 39.

Above the chiller 29 is arranged a blower 30 that sends cool air into the refrigerator, freezer, vegetables, and isolated compartments 2, 3, 4, and 5. On the downstream side of the blower 30, a pressure chamber 32 is provided, and, through outlet ports 31a, 31b, and 31c formed in a duct 31 that communicates with the pressure chamber 32, the cool air is introduced into the freezer compartment 3. The cool air in the freezer compartment 3 returns through a cool air return port 35 to the chiller 29 inside the cool air passage 38.

Moreover, a cool air distribution chamber 17 communicates through a damper 17a with the pressure chamber 32. The cool air distribution chamber 17 communicates with a cool air passage 41 arranged behind the refrigerator compartment 2. The cool air passage 41 is composed of a passage assembly 40 having a heat insulator 42 and a passage cover 43 fitted on the front face thereof. Reference numeral 47 represents an electric circuit assembly for controlling the operation of the refrigerator and of the devices incorporated therein. The electric circuit assembly 47 is enclosed in an electric parts cover 47a.

Figure 2:
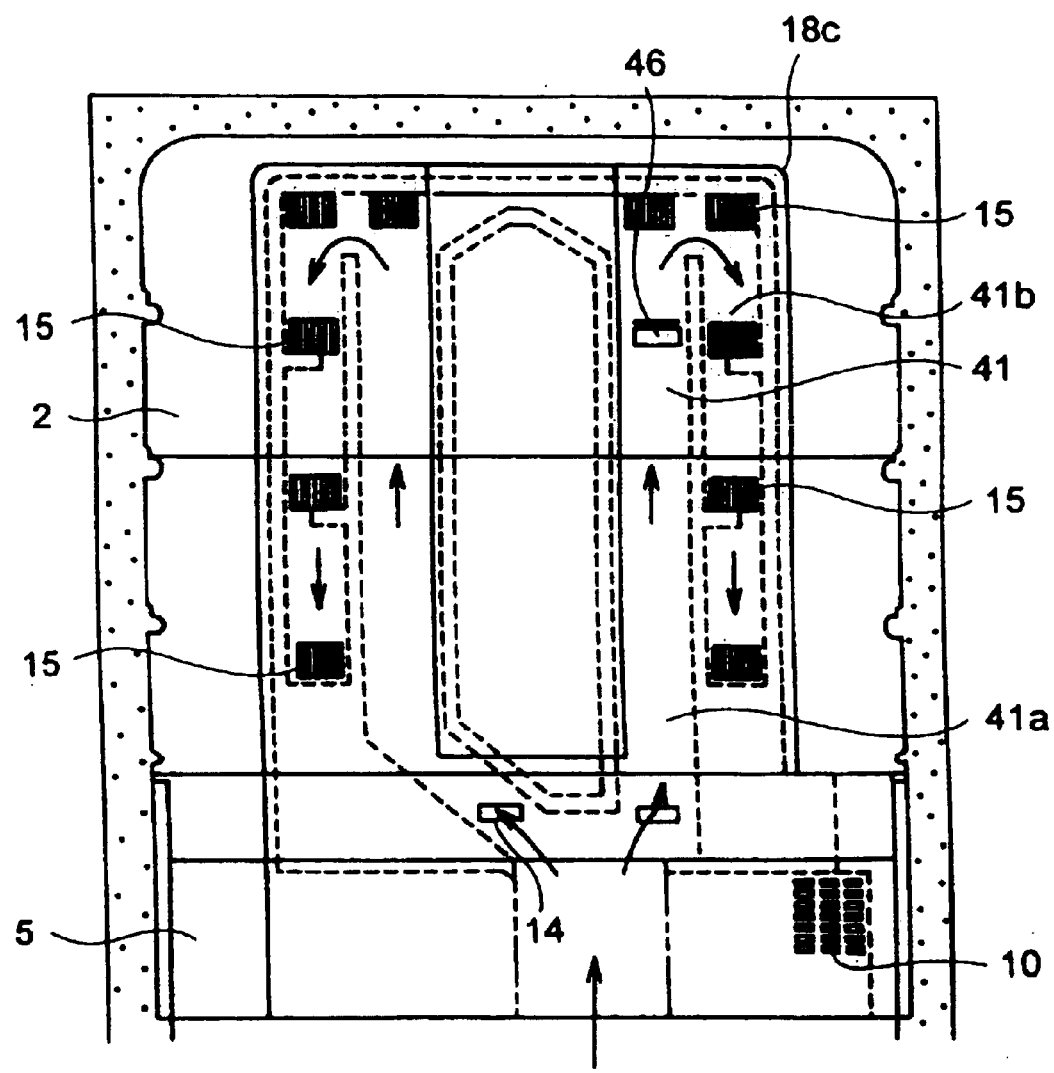
FIG. 2 is a front view of the refrigerator of the first embodiment of the invention.

FIG. 2 shows a front view of the refrigerator compartment 2. The cool air passage 41 consists of upward passages 41a arranged substantially at the center of the refrigerator compartment 2 and downward passages 41b arranged outside the upward passages 41a. The upward and downward passages 41a and 41b communicate with each other at their top ends. The cool air introduced into the cool air passage 41 is sent through an outlet port 14 into the isolated compartment 5.

On the other hand, the rest of the cool air flows upward through the upward passages 41a and enters the downward passages 41b, whence the cool air is sent through outlet ports 15 into the refrigerator compartment 2. In the diagram of the refrigerator compartment 2, in a right-hand lower portion as seen from the front is located a cool air return port 10, consisting of a plurality of holes arranged in a grid-like formation, into which the cool air inside the refrigerator compartment 2 is introduced.

In FIG. 1, behind the cool air return port 10, an ion generation chamber 45 is provided in which ions (a substance that kills bacteria) are generated by corona discharge. Below the ion generation chamber 45 is provided a cool air passage 16 communicating therewith and covered with a heat insulator 16a from around. In this figure, the ion generation chamber 45 and the cool air passage 38 are shown on an identical plane for convenience' sake; in reality, however, the cool air passage 16 and the cool air passage 38 are arranged side by side, and the cool air passage 16 and the ion generation chamber 45 are arranged substantially on an identical plane.

An outlet port 13 is arranged at the bottom end of the cool air passage 16 so as to face inside the vegetables compartment 4. Thus, the cool air flowing through the cool air passage 16 is discharged into the vegetables compartment 4. The cool air in the vegetables compartment 4 is sent through a cool air return port 34 back to the chiller 29 inside the cool air passage 38.

Figure 3:
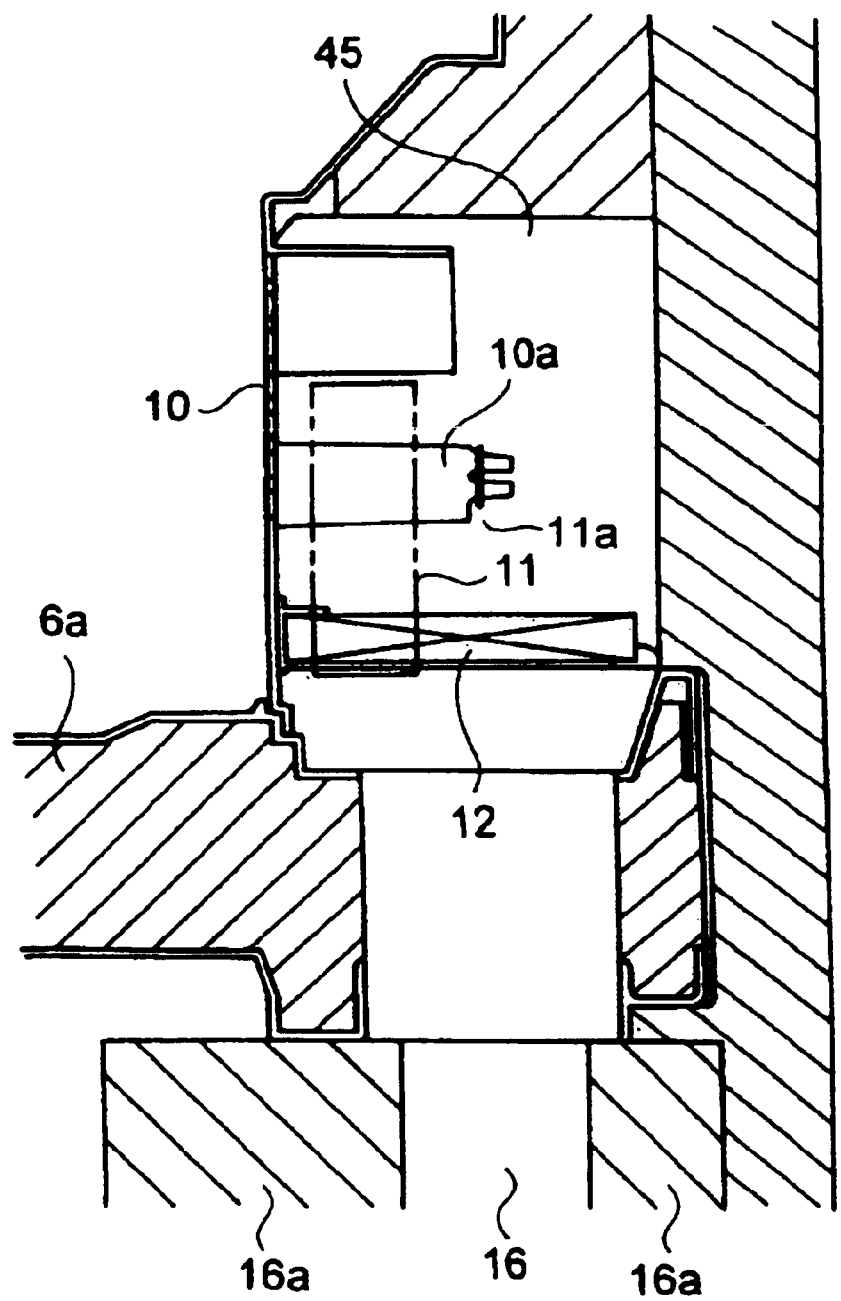
FIG. 3 is a side sectional view of the ion generation chamber of the refrigerator of the first embodiment of the invention.
Figure 4:
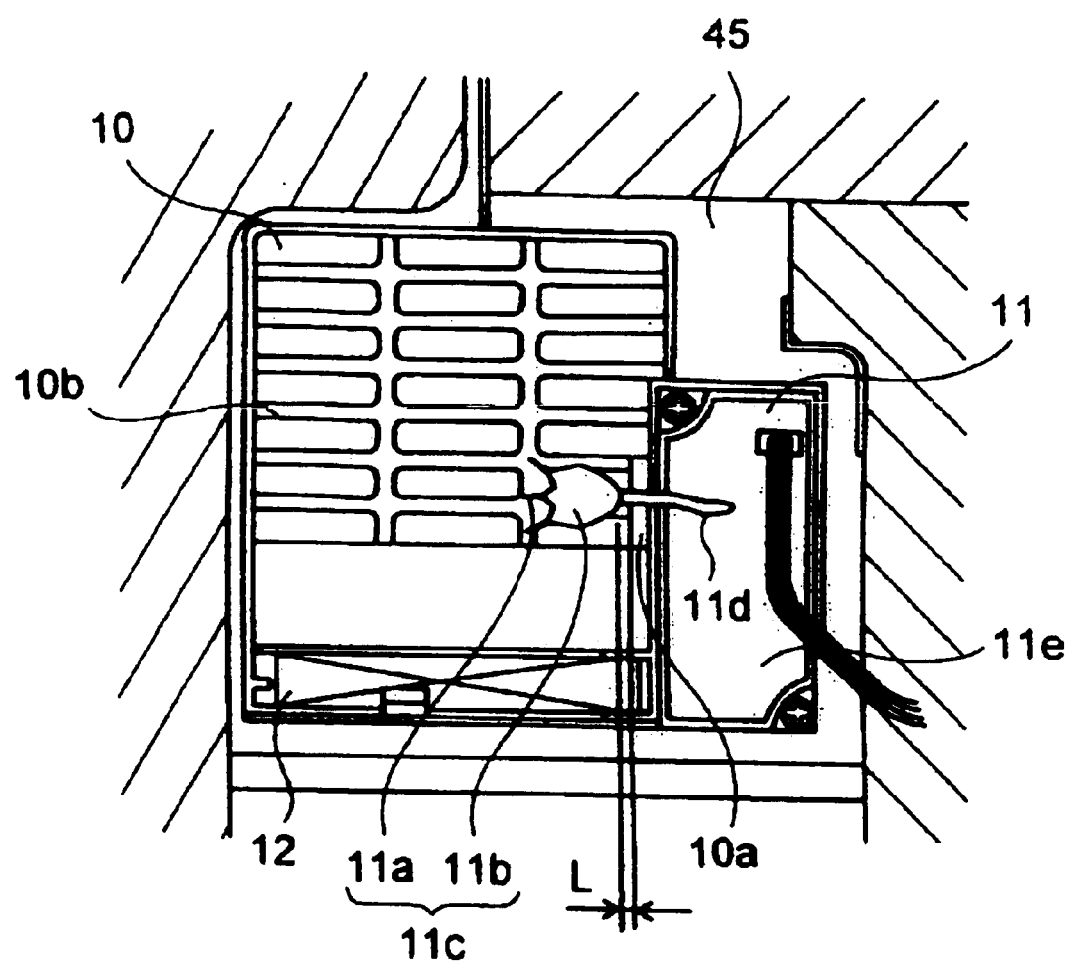
FIG. 4 is a rear view of the ion generation chamber of the refrigerator of the first embodiment of the invention.

FIGS. 3 and 4 are a side sectional view and a rear view, respectively, of the ion generation chamber 45. Inside the ion generation chamber 45, an ion generating device 11 (a sterilizer) having a needle-like electrode 11a is provided. The needle-like electrode 11a is so formed as to protrude from a flat-plate-shaped flat portion 11b, and is connected to a power supply 11e through a lead 11d covered with an insulating coating. The lead 11d is supported on a support 10a made of resin and formed integrally with a grille 10b that forms the cool air return port 10.

The flat portion 11b is arranged parallel to a vertical plane so that, when corona discharge is not taking place, as little dust as possible settles on the needle-like electrode 11a and the flat portion 11b, which together constitute an electrode portion 11c. Moreover, the flat portion 11b is arranged parallel to the grille 10b forming the cool air return port 10. This makes the distance from the cool air return port 10 to each of the pointed tips of the needle-like electrode 11a equal. In this way, it is possible to secure safety against electrical shock hazards without the need for unduly large space.

When a high voltage is applied from the power supply 11e through the lead 11d to the needle-like electrode 11a, electric charge concentrates on the tips of the needle-like electrode 11a, and dielectric breakdown occurs locally at the tips of the electrode 11a in the cool air introduced through the cool air return port 10, permitting corona discharge to take place. The lead 11d is made 200 mm long or shorter to alleviate the lowering of discharge efficiency and to make its wiring easy. By making the lead 11d 100 mm long or shorter, it is possible to further alleviate the lowering of discharge efficiency. Further preferably, by making it 50 mm long or shorter, it is possible to connect the electrode 11a with almost no lowering of discharge efficiency.

As a result of corona discharge, when the applied voltage is positive, positive ions composed mainly of $H^+(H_2O)_n$ are generated and, when the applied voltage is negative, negative ions composed mainly of $O_2^-(H_2O)_m$ are generated. These ions $H^+(H_2O)_n$ and $O_2^-(H_2O)_m$ flock together on the surface of microorganisms, and surround airborne bacteria, such as microorganisms, floating in the air. Then, through the reactions represented by formulae (1) to (3) below, the ions, by colliding with each other, produce radicals [.OH] (hydroxy radicals) and $H_2O_2$ (hydrogen peroxide) on the surface of microorganisms and the like, and thereby kill airborne bacteria.

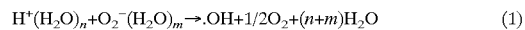

$$H^+(H_2O)_n+O_2^-(H_2O)_m \rightarrow .OH+1/2O_2+(n+m)H_2O \quad (1)$$

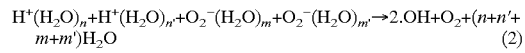

$$H^+(H_2O)_n+H^+(H_2O)_{n'}+O_2^-(H_2O)_m+O_2^-(H_2O)_{m'} \rightarrow 2.OH+O_2+(n+n'+m+m')H_2O \quad (2)$$

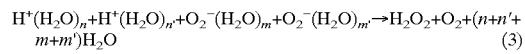

$$H^+(H_2O)_n+H^+(H_2O)_{n'}+O_2^-(H_2O)_m+O_2^-(H_2O)_{m'} \rightarrow H_2O_2+O_2+(n+n'+m+m')H_2O \quad (3)$$

In this embodiment, airborne bacteria floating in the cool air are killed by positive and negative ions. Thus, the stored articles are damaged less than in conventional structures. Moreover, there is provided no electrode such as an opposed electrode that is arranged so as to be opposed to the needle-like electrode 11a or a collecting electrode that collects positive ions. Thus, it never occurs that ions are attracted by such electrodes because of a potential difference, or that ions are generated in the narrow area between the needle-like and opposed electrodes, as in conventional structures.

In this way, it is possible to spared ions in the cool air passage without the need for strong blowing so that airborne bacteria floating in the cool air are caught and killed in a wider area. This enhances the sterilizing effect. Moreover, it is possible to simplify and thereby miniaturize the ion generating device 11.

Moreover, positive and negative voltages are applied to the needle-like electrode 11a, and therefore the electric circuit is not charged with either, without the need for a ground potential. Thus, there is no need for direct grounding to the earth, and therefore the refrigerator 1 can be installed easily in a household. This makes it possible to further simplify and miniaturize the ion generating device 11.

Formulae (1) to (3) above show that equal numbers of positive and negative ions are necessary to produce radicals. However, if positive ions alone make contact with food or the like, they promote the aging of its cells, and therefore, in this embodiment, positive ions are generated in a smaller number than negative ions. As a result, while positive and negative ions flock together on the surface of microorganisms and thereby kill airborne bacteria, the surplus negative ions prevent the proliferation of airborne bacteria and prevent them from flowing into the vegetables compartment.

Here, if the number of positive ions generated is less than 3% of the number of negative ions generated, too little [.OH] is produced, resulting in an unsatisfactory sterilizing effect. Therefore, the number of positive ions generated is set to be 3% of the number of negative ions generated or greater. By generating 5,000 positive ions per cubic centimeter ($cm^3$), it is possible to obtain a satisfactory sterilizing effect.

The numbers of ions of each polarity generated can be varied by varying the periods for which positive and negative voltages are applied. Alternatively, the numbers of ions generated may be controlled by controlling duty factors by varying the periods for which those voltages are kept on and off.

By corona discharge, ozone is generated simultaneously with ions. Since ozone has an oxidizing effect, if it flows in a high concentration into the refrigerator compartment 2 or the vegetables compartment 4, it oxidizes and degrades food. To avoid this, the voltages applied to the needle-like electrode 11a are set to be low (for example, an alternating-current voltage between +1.8 kV and −1.8 kV) so that only trace amounts of ozone is generated by corona discharge. Further preferably, duty factors are controlled in such a way that the turning on and off of the applied voltages is repeated at short time intervals, because this helps alleviate the generation of ozone.

The needle-like electrode 11a is arranged in a cool air passage (the ion generation chamber 45) that communicates with the refrigerator compartment 2. Thus, the cool air that flows into the cool air return port 10 prevents ozone from flowing into the refrigerator compartment 2. Moreover, as will be described later, ozone is eliminated in the cool air passage. This prevents oxidization of food.

Moreover, arranging the needle-like electrode 11a, for example, 40 mm or more behind the cool air return port 10 in the cool air passage eliminates the need to cover the needle-like electrode 11a with an insulating case for safety, and thus helps make the ion generating device 11 inexpensive. In addition, the cool air that flows into the cool air return port 10 prevents ozone, which is generated together with ions, from flowing into the refrigerator compartment 2, and moreover, as will be described later, ozone is eliminated in the cool air passage. This prevents oxidization of food.

The needle-like electrode 11a may be composed of a plurality of needle-like conductors kept at an identical potential. In this case, more ions are discharged from the tip of each conductor along the extension line thereof. Therefore, by arranging a plurality of conductors in such a way that they point in different directions, it is possible to discharge ions in a wide area around the needle-like electrode 11a and thereby enhance the sterilizing effect. The discharged ions then spread further around.

If the distance L between the support 10a and the electrode portion 11c is too short, when condensation collects on the support 10a, there is a risk of a high voltage being applied to the support 10a. To avoid this, the distance L is set to be 3.5 mm or longer (for example, 5 mm), further preferably 10 mm or longer, so as to place the support 10a sufficiently away from the needle-like electrode 11a to obtain secure insulation. Moreover, this also helps widen the area in which ions are discharged by corona discharge and thereby enhance the sterilizing effect. Preferably, the support 10a is made of an insulating material.

When positive and negative ions are generated with a single needle-like electrode 11a, part of the ions cancel each other near the electrode, reducing the effective number of ions generated. Thus, by providing two needle-like electrodes 11a and generating positive and negative ions with the two separate electrodes, it is possible to increase the effective number of ions generated. This also makes it possible to vary easily the number of ions of each polarity generated.

The balance of the numbers of ions of different polarities generated can be varied easily by configuring the two electrodes differently in terms of the circuit configuration used therewith, the voltage applied thereto, the shape and material of the electrodes themselves, and the like. Moreover, by arranging the two electrodes at least 10 mm or more (preferably 30 mm or more) away from each other, it is possible to use the generated ions effectively for sterilization with almost no cancellation between positive and negative ions.

Figure 5:
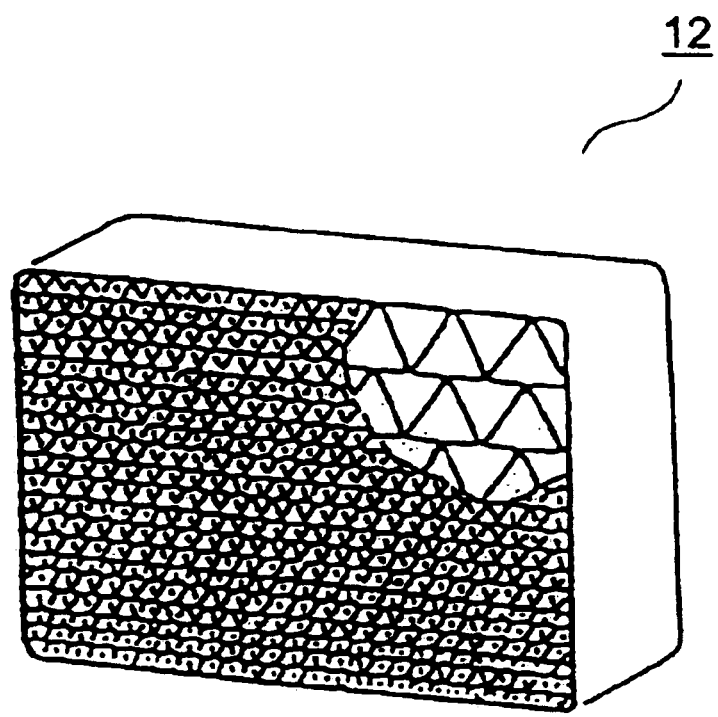
FIG. 5 is a perspective view of the deodorizing device of the refrigerator of the first embodiment of the invention.

Below the needle-like electrode 11a (on the downstream side thereof), a deodorizing device 12 for removing odor-producing substances is arranged. As shown in FIG. 5, the deodorizing device 12 is a corrugated honeycomb structure made of a material coated with a low-temperature deodorizing catalyst and an absorbent. The deodorizing device 12 may be a filter or a nonwoven fabric holding a low-temperature deodorizing catalyst and an absorbent. However, a honeycomb structure is preferable because it helps reduce pressure loss.

The low-temperature deodorizing catalyst and the absorbent catch airborne bacteria as well. Thus, by placing the deodorizing device 12 near the ion generating device 11, it is possible to kill in large numbers the airborne bacteria caught by the deodorizing device 12 and thereby enhance the sterilizing effect. Here, it is preferable to secure a distance of at least 10 mm between the needle-like electrode 11a, from which corona discharge takes place, and the surface of the deodorizing device 12.

The reason is that, if the distance between the needle-like electrode 11a and the deodorizing device 12 is too short, the deodorizing device 12 acts like an opposed electrode and produces a strong electric field. As a result, even when a low voltage (for example, an alternating-current voltage from +1.8 kV to −1.8 kV (3.6 kVp-p) having a frequency of about 90 kHz) is applied, a state similar to one with increased discharge output results, quickening the deterioration of the deodorizing device 12. Thus, by setting the distance to be 10 mm or longer, it is possible to prevent the deterioration of the deodorizing device 12. In particular, when the deodorizing device 12 contains high contents of carbon and metals (for example, activated carbon particles, carbon fiber, platinum powder, nickel, and the like), it deteriorates markedly quickly.

The discharge from the needle-like electrode 11a reaches an area covering a solid angle of $2\pi sr$ mainly in front of each tip thereof, forming an effective discharge area that is hemispherical in shape. For example, applying the aforementioned voltage (3.6 kVp-p) results in an effective discharge area having a radius of 100 mm (100,000 or more negative ions per cubic centimeter ($cm^3$).

Thus, by arranging the deodorizing device 12 inside the effective discharge area, it is possible to achieve a significant sterilizing effect in the deodorizing device 12 and thereby enhance sterilization efficiency. This makes it possible to lower the applied voltage and reduce the amount of ozone generated.

The results of experiments are presented below in which ions were discharged from an ion generating device having a single needle-like electrode 11a, on the assumption that the ions were discharged into a refrigerator with a capacity of 400 L and with cool air circulating therein. Here, the bacteria reduction rate is the ratio of the number of airborne bacteria per unit volume after the discharge of ions to that before the discharge of ions.

| Experiment No. | Voltage Applied | Voltage Application Duration | Bacteria Reduction Rate |
| --- | --- | --- | --- |
| 1 | −1.8 kV to +1.8 kV | 10 minutes | 25% |
| 2 | −2.5 kV to +2.5 kV | 45 minutes | 80% |

In Experiment No. 1, the bacteria reduction rate was 25%, and almost no ozone odor was smelt in sensory testing after the experiment. Thus, by the application of an alternating-current voltage of which the absolute value is 1.8 kV or higher, it is possible to realize a refrigerator that offers a certain sterilizing effect without discomfort. It is to be noted that, for corona discharge to be effective in sterilization, it requires an alternating-current voltage of which the absolute value at its peaks is 1.8 kV.

In Experiment No. 2, the bacteria reduction rate was 80%. On the other hand, about 0.15 mg of ozone was generated, and, in sensory testing, its odor was hardly felt by the user when the door was opened. Thus, by the application of an alternating-current voltage of which the absolute value at its peaks is 2.5 kV, it is possible to realize a refrigerator that offers a sufficient sterilizing effect in a household with a minimum of discomfort.

When the voltage is kept applied for more than 45 minutes, the bacteria reduction rate gradually approaches equilibrium, meaning that, although more ozone is generated, sterilization efficiency lowers. Therefore, it is preferable to apply the voltage for 45 minutes or less at a stretch. Thus, by applying a voltage of 3.6 kVp-p to 5 kVp-p to the needle-like electrode 11a for 10 to 45 minutes at a stretch, it is possible to realize a refrigerator that offers a satisfactory sterilizing effect in ordinary use with a minimum of discomfort due to the odor of ozone.

The numbers of positive and negative ions generated can be adjusted also by adjusting the absolute values of the positive and negative voltages applied. That is, by varying the absolute values of the positive and negative voltages so that they have a peak value of 1.8 kV or higher within the range from 3.6 kVp-p to 5 kVp-p, it is possible to adjust the number of ions of each polarity generated.

Moreover, as shown in FIG. 4 described earlier, by forming the needle-like electrode 11a so as to have three pointed tips, it is possible to maintain the number of ions generated at the desired or even a higher level with a low applied voltage and thereby further enhance the sterilizing effect and reduce the amount of ozone generated. Specifically, in an experiment, a voltage of 3.6 kVp-p to 5 kVp-p was applied to each tip of the needle-like electrode 11a for 15 to 20 minutes and, as in the experiments described above, the produced ions were discharged into a storeroom with a capacity of 400 L. In this experiment, the bacteria reduction rate was 50%, and about 0.05 mg of ozone was generated. In this way, it is possible to realize a refrigerator with a great sterilizing effect with which the user smells hardly any ozone odor when the door is opened.

In addition, by configuring the ion generating device 11 in such a way that its operation, once stopped, is not restarted for a predetermined period thereafter, it is possible to further reduce the amount of residual ozone. For example, when the ion generating device 11 is driven for 30 minutes and is then kept stopped for 30 minutes with the damper 17a open, the amount of residual ozone drops substantially to 0%. This helps further reduce the discomfort due to the odor of ozone.

Moreover, by configuring the ion generating device 11 in such a way that it operates in synchronism with the operation of the compressor 46, it is possible to reduce the amount of ozone when the compressor 46 is stopped and thereby further reduce the discomfort. Here, by opening the damper 17a in synchronism with the starting of the ion generating device 11 and the blower 30, it is possible to discharge ions into the refrigerator compartment and thereby further enhance the sterilizing effect. An operation switch (not shown) for driving the ion generating device 11 is provided, for example, on the outer surface of the refrigerator compartment door 19. This permits the user to drive the ion generating device 11 and perform sterilization whenever he or she so desires.

The bacteria reduction rate can be increased by increasing the number of electrode portions 11c. In an refrigerator for use in an ordinary household, it is preferable to provide one to three electrode portions 11c each having a needle-like electrode 11a with one to five pointed tips.

The low-temperature deodorizing catalyst contains a copper-manganese-based oxide, and thus oxidizes and thereby decomposes amine- and thiol-based volatile substances and odor-producing substances such as hydrogen sulfide. Moreover, a copper-manganese-based oxide functions also as an ozone decomposing catalyst, and thus serves to decompose ozone.

In this way, it is possible to reduce the discharge of ozone without separately providing an ozone removing device, and thus, as the driving of the ion generating device is controlled in the manner described later, it is possible to reduce the ozone concentration in the refrigerator and vegetables compartments to a negligible level that is harmless to the human body. Moreover, the omission of an ozone removing device helps reduce the cost of the refrigerator 1. The deodorizing device 12 is arranged near the ion generating device 11, and therefore the generated ozone is decomposed quickly so as not to affect the other components, the refrigerator compartment 2, and the like.

In a case where a deodorizing effect is obtained by another method such as by heat deodorizing, the deodorizing device 12 may hold an ozone decomposing catalyst that effectively decomposes ozone. Examples of such ozone decomposing catalysts include manganese dioxide, platinum powder, lead dioxide, copper (II) oxide, and nickel.

The absorbent serves to absorb odor-producing substances, ozone, and airborne bacteria, and contains, for example, silica gel, activated carbon, zeolite, sepiolite, or the like. An absorbent in the form of particles or powder may be provided separately. Detachably arranging the deodorizing device 12 makes its replacement and cleaning possible, and thus helps keep the inside of the refrigerator clean.

Arranging the deodorizing device 12 on the upstream side of the ion generating device 11 prevents ions from making contact with the low-temperature deodorizing catalyst and the absorbent and thereby losing their ionicity. This helps widen the area in which ions are present and thereby enhance the sterilizing effect. In this way, the deodorizing device 12 may be arranged to suit the purpose of providing it.

In the refrigerator structured as described above, the cool air cooled by the chiller 29 is sent through the cool air passage 38 into the pressure chamber 32 by the blower 30. The cool air then flows out of the pressure chamber 32 through the duct 31, and is then discharged into the freezer compartment 3 through the outlet ports 31a, 31b, and 31c. Thus, the inside of the freezer compartment 3 is cooled. The cool air then flows in front of the freezer cases 23 and 24 and then below the freezer case 24 so as to return, through the cool air return port 35, to the chiller 29.

When the temperature inside the refrigerator compartment 2 is detected being higher than a predetermined temperature by a refrigerator compartment temperature sensor 48 (see FIG. 2) provided in the refrigerator compartment 2, the damper 17a of the cool air distribution chamber 17 is opened. The cool air in the pressure chamber 32 is introduced through the cool air distribution chamber 17 into the cool air passage 41.

Part of the cool air passing through the cool air passage 41 is sent through the outlet port 14 into the case 7 of the isolated compartment 5 to cool the articles stored in the case 7, and then flows between the top of the front end of the case 7 and the shelf 8d into the refrigerator compartment 2. Here, the rate at which the cool air is sent through the outlet port 14 into the case 7 is adjusted by adjusting the open areas of the outlet ports 14 and 15 in such a way that the temperature inside the case 7 is kept lower than that inside the refrigerator compartment 2.

The rest of the cool air passing through the cool air passage 41 flows upward in the upward passages 41a, then flows downward in the downward passages 41b, and is then discharged through the outlet port 15 into the refrigerator compartment 2. The cool air flows downward while cooling the articles put on the shelves 8a to 8d and in the door pockets 21a to 21d. Then, the cool air, together with the cool air that has flowed out of the isolated compartment 5, passes between the bottom of the case 7 and the partition 6a and flows through the cool air return port 10 into the ion generation chamber 45.

A guide portion may be provided in front of the cool air return port 10 so as to cover the cool air return port 10 and be open below the case 7. This prevents short-circuiting of the cool air from the outlet port 14 to the cool air return port 10, and makes it possible to suck the cool air in a laterally wide area below the case 7 and thereby obtain a uniform flow of cool air. This helps enhance the cooling efficiency inside the refrigerator compartment 2.

The cool air that has flowed into the ion generation chamber 45 reaches around the needle-like electrode 11a of the ion generating device 11. The positive and negative ions generated as a result of corona discharge taking place from the needle-like electrode 11a flock together and surround airborne bacteria floating in the cool air, and the resulting radicals such as [.OH] and $H_2O_2$ kill the airborne bacteria. Thereafter, the deodorizing device 12 decomposes or absorbs and thereby removes the odor-producing substances emitted from articles stored in the isolated compartment 5 and the refrigerator compartment 2 and the ozone generated in trace amounts by corona discharge.

The cool air that has circulated in the isolated compartment 5 and the refrigerator compartment 2 flows through the cool air return port 10 and passes by the needle-like electrode 11a arranged close to the cool air return port 10 and then through the deodorizing device 12. This makes it possible to quickly destroy the strong smell of fish or the like put in the isolated compartment 5, and to efficiently destroy, near their sources, many smells emitted from articles stored in the refrigerator compartment 2, which is kept at a relatively high temperature. This alleviates the passing of smells inside the isolated compartment 5 and the refrigerator compartment 2 to other places.

The deodorizing device 12 may be arranged between the case 7 and the partition 6b. This requires an ozone removing device to be provided separately, but helps widen the area through which the cool air passes and thereby enhance the deodorizing effect.

The cool air that has passed through the deodorizing device 12 flows through the cool air passage 16 and is then discharged through the outlet port 13 into the vegetables compartment 4. This cool air is cool air that has returned from the refrigerator compartment 2, but is deodorized by the ion generating device 11 and the deodorizing device 12, and therefore no smell passes to articles stored in the vegetables compartment 4.

The cool air then flows below and then in front of the vegetables case 26 in the vegetables compartment 4, then flows on the top surface of the vegetables case cover 28, and then flows through the cool air return port 34 into the cool air passage 38. The defrosting heater 33 is coated with a catalyst coating layer holding a deodorizing catalyst, so that the order-producing substances present in the cool air that has passed through the vegetables compartment 4 are removed by the heater 33. The cool air then returns to the chiller 29.

Positive and negative ions may be discharged directly into the refrigerator compartment 2 or the vegetables compartment 4, which is part of the cool air flow passage. This makes it possible to kill airborne bacteria more effectively.

Figure 6:
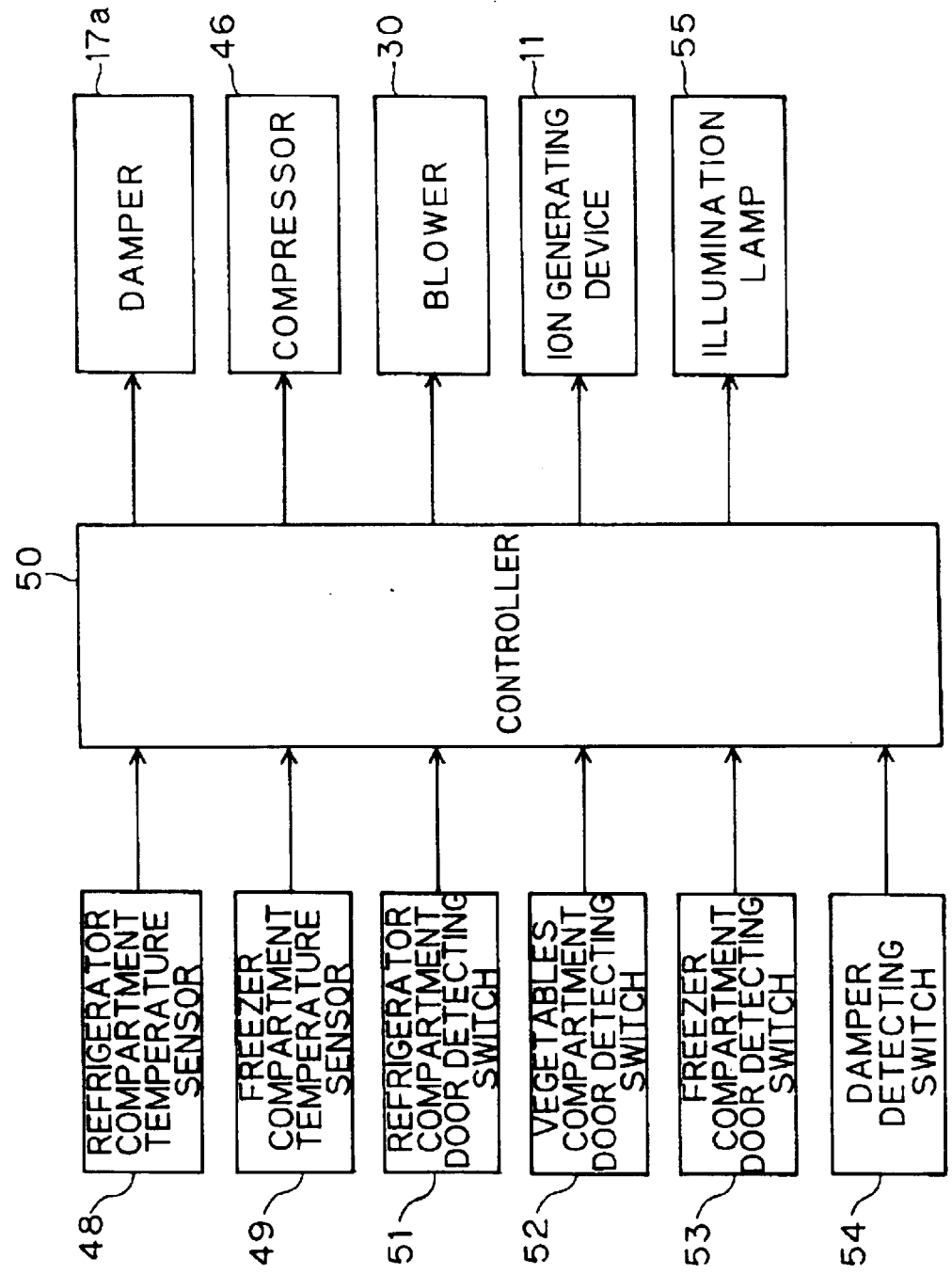
FIG. 6 is a block diagram showing the configuration of the refrigerator of the first embodiment of the invention.

FIG. 6 is a block diagram showing the configuration of the refrigerator 1. The electric circuit assembly 47 (see FIG. 1) includes a controller 50 realized with, for example, a microcomputer. The controller 50 is fed with the temperatures inside the refrigerator compartment 2 and the freezer compartment 3 detected by the refrigerator compartment temperature sensor 48 (see FIG. 2) and a freezer compartment temperature sensor 49.

A refrigerator compartment door detecting switch 51, a vegetables compartment door detecting switch 52, and a freezer compartment door detecting switch 53 check whether the refrigerator compartment door 19, the vegetables compartment door 25, and the freezer compartment door 22 are open or closed, and feeds the results of checking to the controller 50. Moreover, a damper detecting switch 54 checks whether the damper 17a is open or closed, and feeds the result of checking to the controller 50.

Moreover, to the controller 50 are also connected the damper 17a, the compressor 46, the blower 30, the ion generating device 11, and an illumination lamp 55. The controller 50, on the basis of signals fed thereto, controls the driving of these components.

Figure 7:
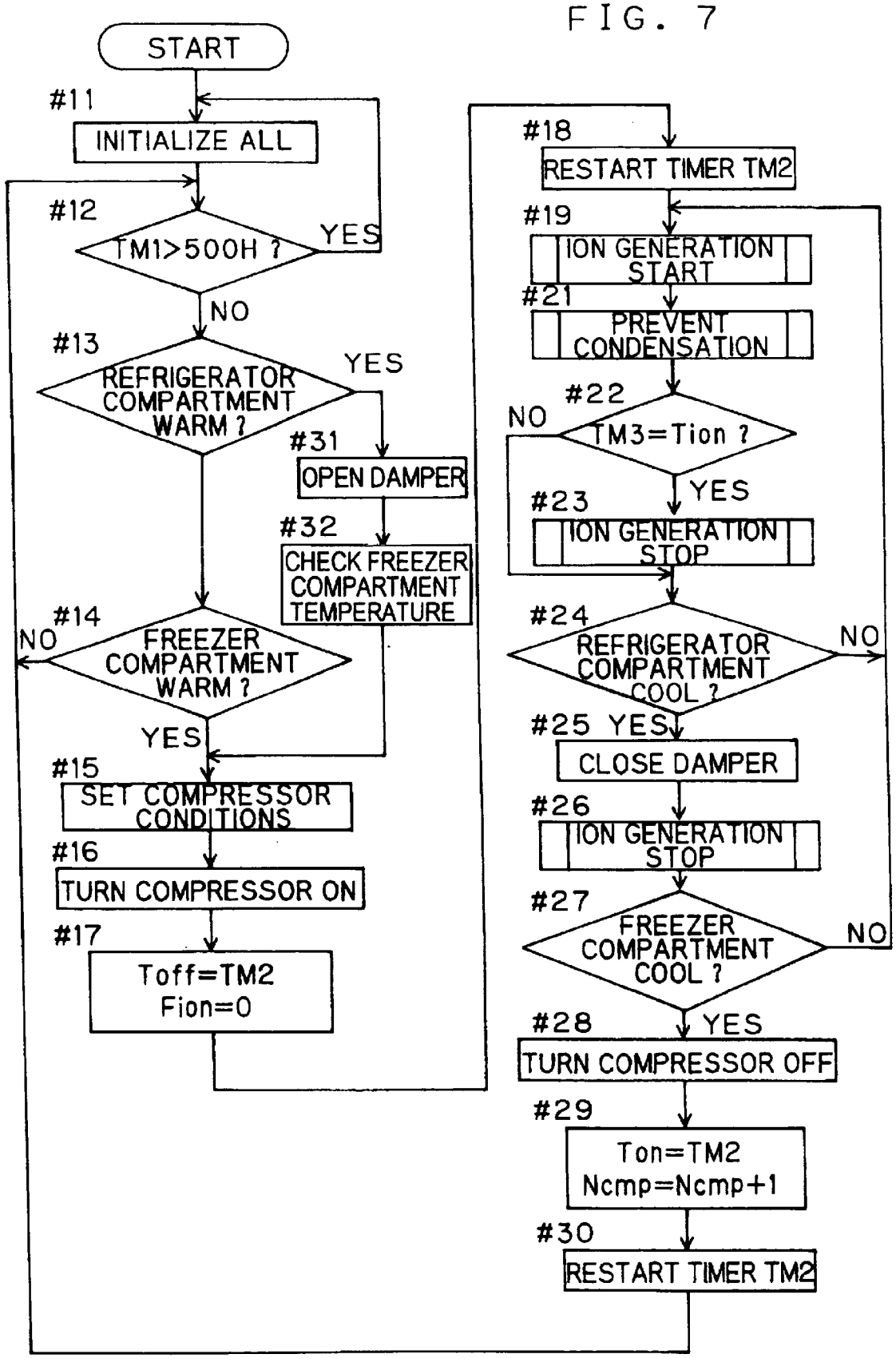
FIG. 7 is a flow chart illustrating the operation of the refrigerator of the first embodiment of the invention.
Figure 8:
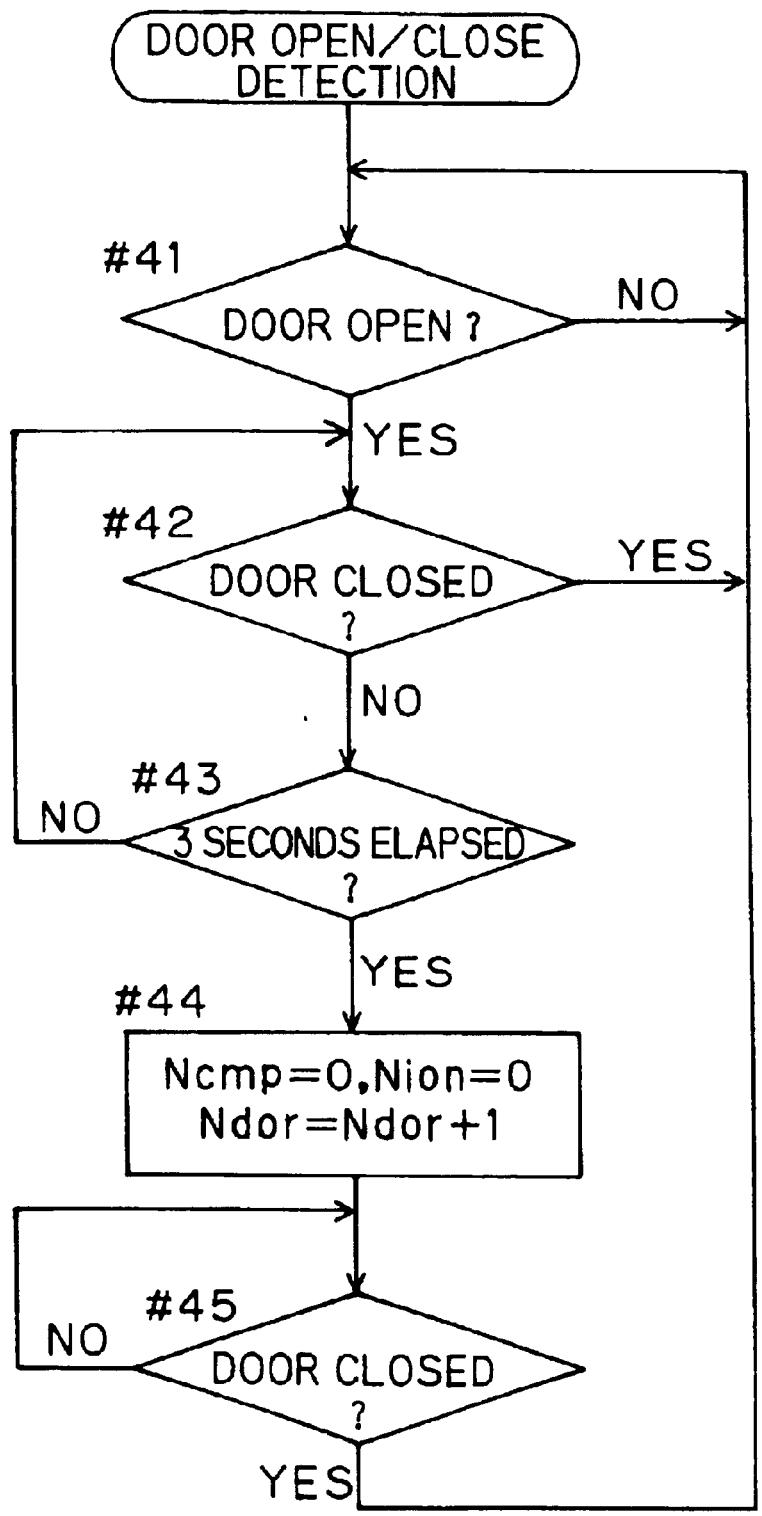
FIG. 8 is a flow chart illustrating the operation for door open/closed detection of the refrigerator of the first embodiment of the invention.

The ion generating device 11 is driven according to the states of the refrigerator compartment door 19, the vegetables compartment door 25, and the damper 17a, the operation status of the compressor 46, and the like. FIG. 7 is a flow chart of the main routine of the operation of these components. FIG. 8 shows the subroutine, i.e. a door open/close detection procedure, for constantly checking whether the refrigerator compartment door 19 and the vegetables compartment door 25 are open or closed.

In FIG. 8, in step #41, whether one of the refrigerator compartment door 19 and the vegetables compartment door 25 is open or not is checked, and the flow waits until one of them is opened. When the refrigerator compartment door 19 or the vegetables compartment door 25 is opened, the damper 17a is closed, and a timer TM3 and the ion generating device 11 are halted temporarily. In step #42, whether the refrigerator compartment door 19 and the vegetables compartment door 25 are closed or not is checked.

If they are not closed, then, in step #43, whether or not three seconds has elapsed after the refrigerator compartment door 19 or the vegetables compartment door 25 was opened is checked. If three seconds has not yet elapsed, the flow returns to step #42 so that steps #42 and #43 are repeated. If the refrigerator compartment door 19 or the vegetables compartment door 25 is opened earlier than three seconds has elapsed, the flow returns to step #41, where it waits until the refrigerator compartment door 19 or the vegetables compartment door 25 is opened.

When three seconds has elapsed after the refrigerator compartment door 19 or the vegetables compartment door 25 was opened, the flow proceeds to step #44. In step #44, the driving frequencies Ncmp and Nion, which represent how many times the compressor 46 and the ion generating device 11 were driven while the refrigerator compartment door 19 and the vegetables compartment door 25 was closed, are reset, and the open/close frequency Ndor, which represents how many times the refrigerator compartment door 19 or the vegetables compartment door 25 was opened and closed, is incremented. Then, in step #45, the flow waits until the refrigerator compartment door 19 and the vegetables compartment door 25 are closed. When they are closed, the flow returns to step #41, where whether the refrigerator compartment door 19 or the vegetables compartment door 25 is open or not is checked. When the refrigerator compartment door 19 and the vegetables compartment door 25 are closed, the damper 17a is opened, and the ion generating device 11 is restarted. It is to be noted that the checking of whether the refrigerator compartment door 19 and the vegetables compartment door 25 are opened and closed and the checking of whether three seconds has elapsed or not are performed individually for each of these doors.

As will be described later, the driving frequency Ncmp of the compressor 46 is incremented every time the compressor 46 is driven after one of the doors is opened and closed (see FIG. 7, step #17). The driving frequency Nion of the ion generating device 11 is incremented every time the ion generating device 11 is driven after one of the doors is opened and closed (see FIG. 10, step #73). The flow may include the checking of whether another door, for example the freezer compartment door 22, is open or closed. This applies also to the flow charts that will described later.

If the driving frequency Ncmp of the compressor 46, the driving frequency Nion of the ion generating device 11, and the open/close frequency Ndor indicate a risk of too much ozone being accumulated in the refrigerator compartment 2, the vegetables compartment 4, and other storage compartments, the driving of the ion generating device 11 is restrained. Therefore, when the refrigerator compartment door 19 or the vegetables compartment door 25 is kept open for three seconds or longer, it is assumed that part of the air inside the storage compartments has been replaced with outside air, and thus that part of the ozone inside the storage compartments has flowed out. Thus, the driving frequencies Ncmp and Nion are reset. In this way, it is possible to prevent accumulation of too much ozone inside the storage compartments and thereby alleviate the discomfort to the user.

Next, with reference to FIG. 7, how the compressor 46 and other components are driven will be described. When power starts being supplied to the refrigerator 1, then, in step #11, the controller 50 is brought into an initial state so that variables and timers, which will be described later, are initialized. In step #12, whether a timer TM1, which will be described later, has counted 500 hours or not is checked.

Here, the timer has not yet counted so many hours, and therefore the flow proceeds to step #13, where whether the temperature inside the refrigerator compartment 2 detected by the refrigerator compartment temperature sensor 48 is higher than a predetermined temperature or not is checked.

If the temperature inside the refrigerator compartment 2 is higher than the predetermined temperature, then, in step #31, the damper 17a is opened, and then, in step #32, the temperature inside the freezer compartment 3 is detected by the freezer compartment temperature sensor 49. If the temperature inside the refrigerator compartment 2 is equal to or lower than the predetermined temperature, then, in step #14, whether the temperature inside the freezer compartment 3 detected by the freezer compartment temperature sensor 49 is higher than a predetermined temperature or not is checked.

If the temperature inside the freezer compartment 3 is higher than the predetermined temperature, the flow proceeds to step #15. If the temperature inside the freezer compartment 3 is equal to or lower than the predetermined temperature, the flow returns to step #12, and repeats steps #12 to #14 to wait until the temperature inside the refrigerator compartment 2 or the freezer compartment 3 becomes higher than the predetermined temperature.

In step #15, according to the temperatures inside the refrigerator compartment 2 and the freezer compartment 3, the conditions under which to operate the compressor 46 are determined. For example, if the temperatures inside the refrigerator compartment 2 and the freezer compartment 3 are higher than the predetermined set temperatures, the compressor 46 is operated at its full power. In step #16, the compressor 46 is driven under the set conditions to perform a refrigerating cycle. In step #17, the flag Fion indicating the driving of the ion generating device is reset. At this point, to store the period for which the compressor 46 has thus far been kept off, the value of a timer TM2 is substituted in the off period Toff.

When the ion generating device 11 is driven while the compressor 46 is being driven, "1" is substituted in the flag Fion. The off period Toff is used to calculate the operation rate E of the compressor 46. Specifically, using the on period Ton and the off period Toff of the compressor 46, its operation rate E is given by Ton/(Ton+Toff)×100%. Here, where the refrigerator has just started operating, the on period Ton is not determined yet, and therefore the operation rate E cannot be calculated. In step #18, the timer TM2 is restarted to start counting the on period of the compressor 46.

Figure 9:
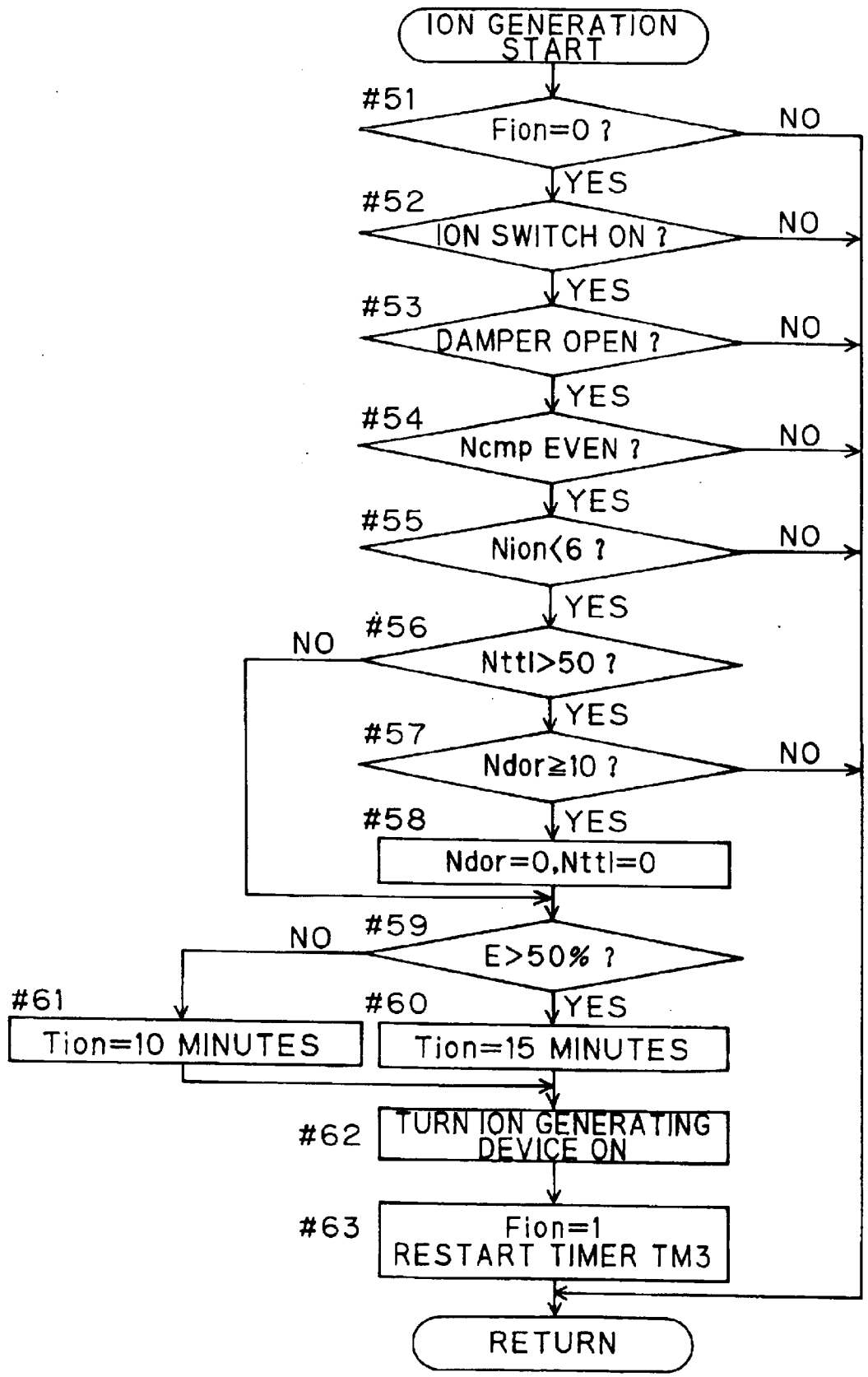
FIG. 9 is a flow chart illustrating the operation for starting ion generation of the refrigerator of the first embodiment of the invention.

In step #19, the flow calls the ion generation starting procedure shown in FIG. 9. In FIG. 9, in step #51, whether the ion generating device driving flag Fion is "0" or not is checked, and, if it is "1," the flow returns to the main routine shown in FIG. 7. In step #52, whether an ion switch (not shown) provided to permit the discharge of ions is set in the on position by the user or not is checked. If the discharge of ions is not permitted, the flow returns to the main routine. In step #53, whether the damper 17a is open or not is checked, and, if it is closed, cool air is not discharged into the freezer compartment 3 and the vegetables compartment 4, and thus ions are not generated, with the flow returning to the main routine.

In step #54, whether or not the driving frequency Ncmp of the compressor 46 is "0" or an even number is checked. If the driving frequency Ncmp is "0," it means that the compressor 46 has not yet been driven after the refrigerator compartment door 19 or the vegetables compartment door 25 was opened and closed.

In this embodiment, ions are generated, in principle, every second time that the compressor 46 is driven after the refrigerator compartment door 19 or the vegetables compartment door 25 was opened and closed. Thus, if the driving frequency Ncmp of the compressor 46 is an even number, the flow proceeds to step #55 and, if the driving frequency Ncmp is an odd number, the flow returns to the main routine. In this way, as long as the refrigerator compartment door 19 or the vegetables compartment door 25 is kept closed after being opened and closed, it is assumed that killing airborne bacteria once is sufficient to keep the number of airborne bacteria low. This prevents the generation of ozone resulting from the generation of more ions than are necessary.

It is also possible to prevent the generation of ozone by generating ions, for example, every third time that the compressor 46 is driven. In this case, in step #54, if the driving frequency Ncmp of the compressor 46 is a multiple of 3, the flow proceeds to step #55.

In step #55, whether the driving frequency Nion of the ion generating device 11 after the refrigerator compartment 2 or the vegetables compartment 4 was opened and closed is smaller than 6 or not is checked. If the driving frequency Nion is 6, it means that the ion generating device 11 was driven 6 times with the refrigerator compartment 2 and the vegetables compartment 4 kept closed, and thus it is assumed that too much ozone has accumulated in the refrigerator compartment 2 and the vegetables compartment 4. Thus, ions are not generated, and the flow returns to the main routine. It is also possible to return to the main routine without generating ions when the period for which the ion generating device 11 has been being driven with the refrigerator compartment 2 and the vegetables compartment 4 kept closed is longer than a predetermined period. Alternatively, it is also possible to check whether or not a predetermined period (for example, three hours) has elapsed with the refrigerator compartment door 19 and the freezer compartment door 22 kept closed after one of them was opened and closed and, if the predetermined period has elapsed, return to the main routine without generating ions.

In step #56, whether the cumulative driving frequency Nttl of the ion generating device 11 is greater than a predetermined number (for example, 50 times in this embodiment) or not is checked, and, if it is smaller, the flow proceeds to step #59. The cumulative driving frequency Nttl is incremented every time the ion generating device 11 is driven, irrespective of whether the refrigerator compartment 2 or the vegetables compartment 4 is open or closed (see FIG. 10, step #73).

Thus, when the open/close frequency Ndor of the refrigerator compartment door 19 or the vegetables compartment door 25 is smaller than a predetermined number (for example, 10 times here) after the ion generating device 11 was driven 50 times on a cumulative basis, it is assumed that too much ozone has accumulated in the refrigerator compartment 2 and the vegetables compartment 4, and thus the flow returns to the main routine without generating ions (setp #57). If the open/close frequency Ndor is 10 or more, then, in step #58, the cumulative driving frequency Nttl and the open/close frequency Ndor are reset, and the flow proceeds to step #59. It is also possible to make a judgement according to, instead of the cumulative driving frequency Nttl, the cumulative period for which the ion generating device 11 has been driven.

In step #59, the operation rate E of the compressor 46 when it was driven last time is calculated, and whether the operation rate E is greater than 50% or not is checked. As described earlier, using the on period of the compressor 46 when it was driven last time and the off period after it stopped being driven last time until it starts being driven this time, the operation rate E is given by Ton/(Ton+Toff)×100%.

If the operation rate E of the compressor 46 is, for example, higher than 50%, then, in step #60, the driving period Tion of the ion generating device 11 is set to be 15 minutes. If the operation rate E of the compressor 46 is 50% or lower, it is considered that the temperature outside is low or the load is light; that is, it is assumed that only a small number of airborne bacteria flow into the refrigerator compartment 2 or the vegetables compartment 4, and thus, in step #61, the driving period Tion of the ion generating device 11 is set to be 10 minutes. In this way, by varying the driving period Tion of the ion generating device 11, it is possible to adjust the number of ions generated so as to reduce the amount of ozone generated by not generating more ions than are necessary.

Here, the generation of a predetermined number of ions is achieved by driving the ion generating device 11 for a predetermined driving period Tion. However, this may be achieved by applying different voltages (for example, a voltage of 5 kVp-p for 10 minutes when E>50% and a voltage of 3.6 kVp-p for ten minutes when E≦50%) to the needle-like electrode 11a.

In step #62, the ion generating device 11 is turned on according to the settings made in steps #60 and #61. In step #63, "1" is substituted in the flag Fion, and the timer TM3 is restarted. The timer TM3 counts the driving period of the ion generating device 11. The flow then returns to the main routine. The aforementioned relationship between the operation rate E and the ion generation period Tion may be defined in more than two steps, for example Tion=7 minutes when E<40%, Tion=10 minutes when 40%≦E<80%, and Tion=15 minutes when E≧80%. This makes finer control of sterilization possible.

Figure 11:
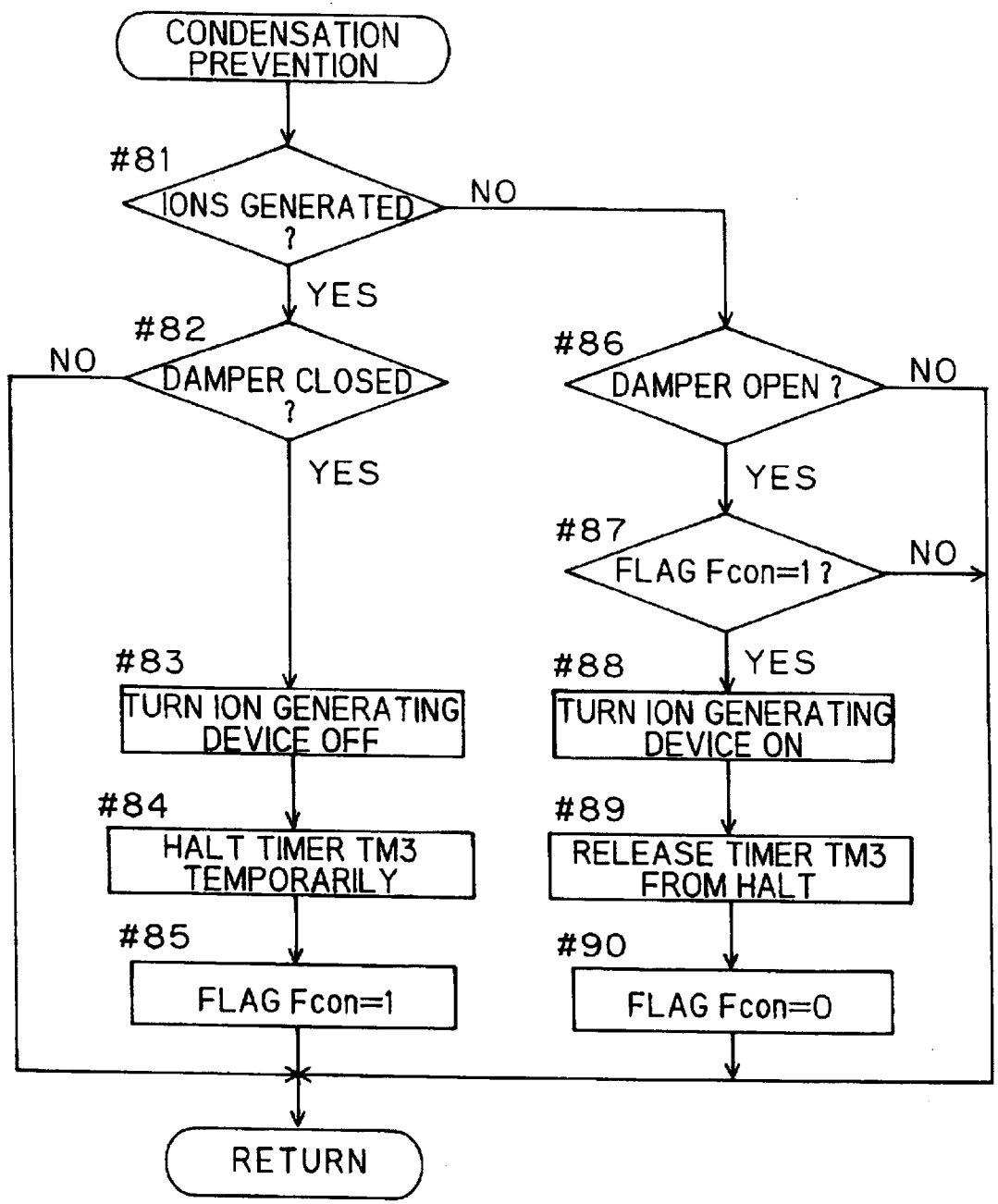
FIG. 11 is a flow chart illustration the operation for condensation prevention of the refrigerator of the first embodiment of the invention.

In the main routine shown in FIG. 7, in step #21, the flow calls the damper freezing prevention procedure shown in FIG. 11. In this embodiment, to prevent the freezing of the damper 17a, when a predetermined period (for example, 12 minutes) elapses after the damper 17a is opened, the damper 17a is closed temporarily.

In the damper freezing prevention procedure, in step #81, whether the ion generating device 11 is being driven or not is checked. If it is being driven, then, in step #82, whether the damper 17a is closed or not is checked. If the damper 17a is open, the damper freezing prevention procedure is not being performed, and thus the flow returns to the main routine.

If the damper 17a is closed, then, in step #83, the ion generating device 11 is stopped. In step #84, the timer TM3 is halted temporarily. In step #85, "1" is substituted in the flag Fcon that indicates the condensation prevention state.

If, in step #81, the ion generating device 11 is found not being driven, then, in step #86, whether the damper 17a is open or not is checked. If the damper 17a is closed, the ion generating device 11 can be left off, and thus the flow returns to the main routine. If the damper 17a is open, then, in step #87, whether the flag Fcon is "1" or not is checked.

If the flag Fcon is "0," it indicates the ordinary ion generation state. Thus, the flow returns to the main routine without performing the rest of the condensation prevention procedure. If the flag Fcon is "1," it indicates that the damper 17a is opened in the damper freezing prevention state, i.e. that the damper freezing prevention procedure is now complete. Thus, in step #88, the ion generating device 11 is driven. In step #89, the timer TM3 is released from the temporary halt. In step #90, the flag Fcon is reset, and the damper freezing prevention state is canceled. As a result, ions, of which the number has not reached the desired number because of the temporary halt, are now produced continuously, making it possible to kill airborne bacteria satisfactorily.

Back in the main routine shown in FIG. 7, in step #22, whether the timer TM3 has counted the set driving time Tion or not is checked. If the timer TM3 has counted the set driving time Tion, then, in step #23, the flow calls the ion generation stopping procedure shown in FIG. 10.

If the timer TM3 has not counted the set driving time Tion, then, in step #24, whether the temperature inside the refrigerator compartment 2 measured by the refrigerator compartment temperature sensor 48 (see FIG. 2) has dropped to a predetermined temperature or not is checked. If the temperature there has not dropped below the predetermined temperature, the flow returns to step #19, and repeats steps #19 to #24.

If the temperature inside the refrigerator compartment 2 has dropped below the predetermined temperature, then, in step #25, the damper 17a is closed. Then, in step #26, the flow calls the ion generation stopping procedure and then, in step #27, whether the temperature inside the freezer compartment 3 has dropped to a predetermined temperature or not is checked. If the temperature inside the freezer compartment 3 has not dropped below the predetermined temperature, the flow returns to step #19, and repeats steps #19 to #26.

If the flag Fion is "1" when the flow returns to step #19, the flow, as soon as it calls the ion generation starting procedure (see FIG. 9), leaves it in step #51. On the other hand, when the refrigerator compartment door 19 or the vegetables compartment door 25 is opened and closed, the driving frequency Ncmp of the compressor 46 and the driving frequency Nion of the ion generating device 11 are reset (see FIG. 8, step #44).

Thus, if the flag Fion is "0," and if the necessary conditions are satisfied in steps #54 and #55 in FIG. 9, the ion generating device 11 may be driven. In this way, when the refrigerator compartment door 19 or the vegetables compartment door 25 is opened and closed and thus it is assumed that at least part of the ozone that has accumulated in the refrigerator compartment 2 and the vegetables compartment 4 has flowed out, the ion generating device 11 is driven immediately to kill airborne bacteria in the refrigerator compartment 2 and the vegetables compartment 4.

Figure 10:
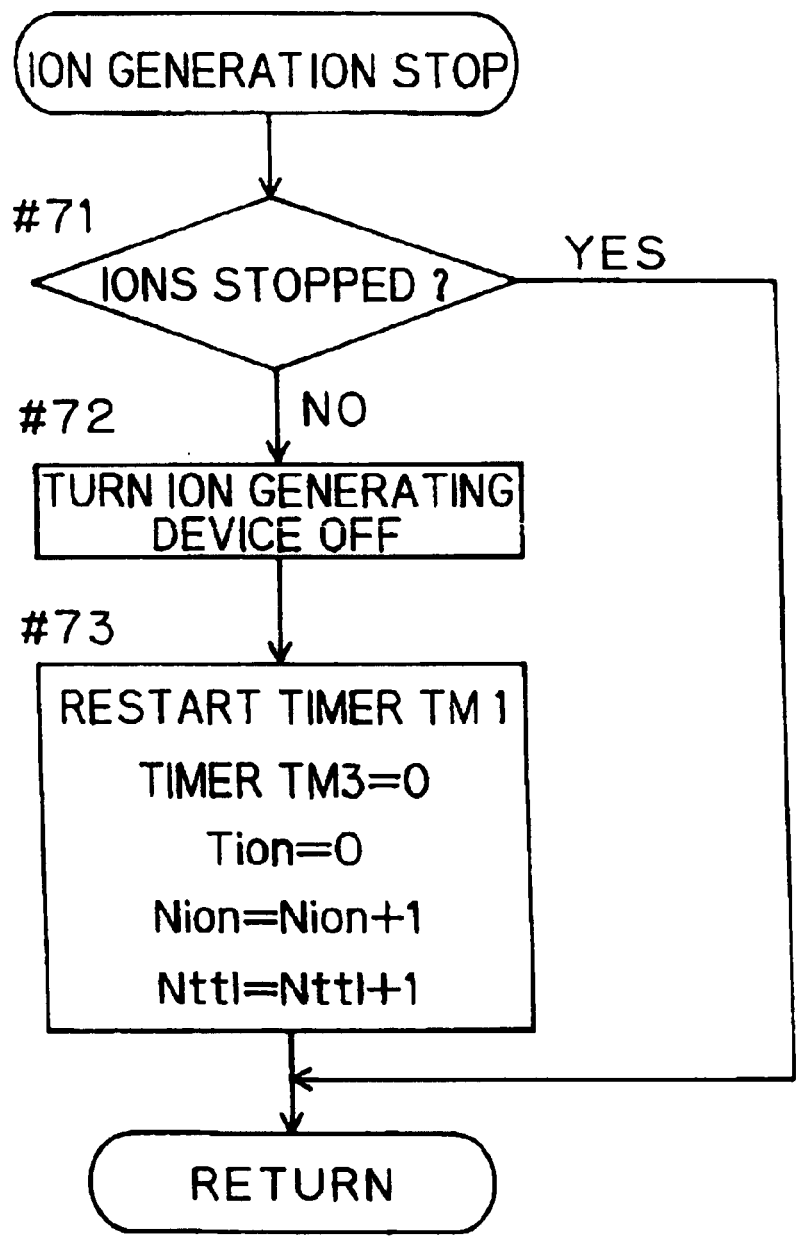
FIG. 10 is a flow chart illustrating the operation for stopping ion generation of the refrigerator of the first embodiment of the invention.

In steps #23 and #26, the flow calls the ion generation stopping procedure shown in FIG. 10. In step #71, whether the generation of ions has already been stopped or not is checked and, if it has already been stopped, the flow returns to the main routine. If ions are still being generated, then, in step #72, the ion generating device 11 is stopped.

In step #73, the timer TM1 is restarted to start counting the period after the ion generating device 11 stopped being driven. Moreover, the timer TM3 and the set driving period Tion of the ion generating device 11 are reset. Moreover, the driving frequency Nion and the cumulative driving frequency Nttl of the ion generating device 11 are incremented, and the flow returns to the main routine.

If the timer TM3 reaches the set driving period Tion before the temperature inside the refrigerator compartment 2 drops to the predetermined temperature, then, in step #23, the ion generating device 11 is stopped. If the temperature inside the refrigerator compartment 2 drops to the predetermined temperature before the timer TM3 reaches the set driving period Tion, then, in step #26, the ion generating device 11 is stopped.

When the ion generating device 11 is stopped in step #26, since the set driving period Tion of the ion generating device 11 has already been reset, after the temperature inside the refrigerator compartment 2 drops to the predetermined temperature, even if the set driving period Tion has not been reached, the ion generating device 11 is kept stopped so as not to generate ions.

When the temperature inside the refrigerator compartment 2 drops quickly, it is assumed that the temperature outside is low, and thus that only a small number of airborne bacteria enter the refrigerator 1. Thus, it is possible to achieve satisfactory sterilization even with the ion generating device 11 stopped while minimizing the increase in the ozone level.

Figure 12:
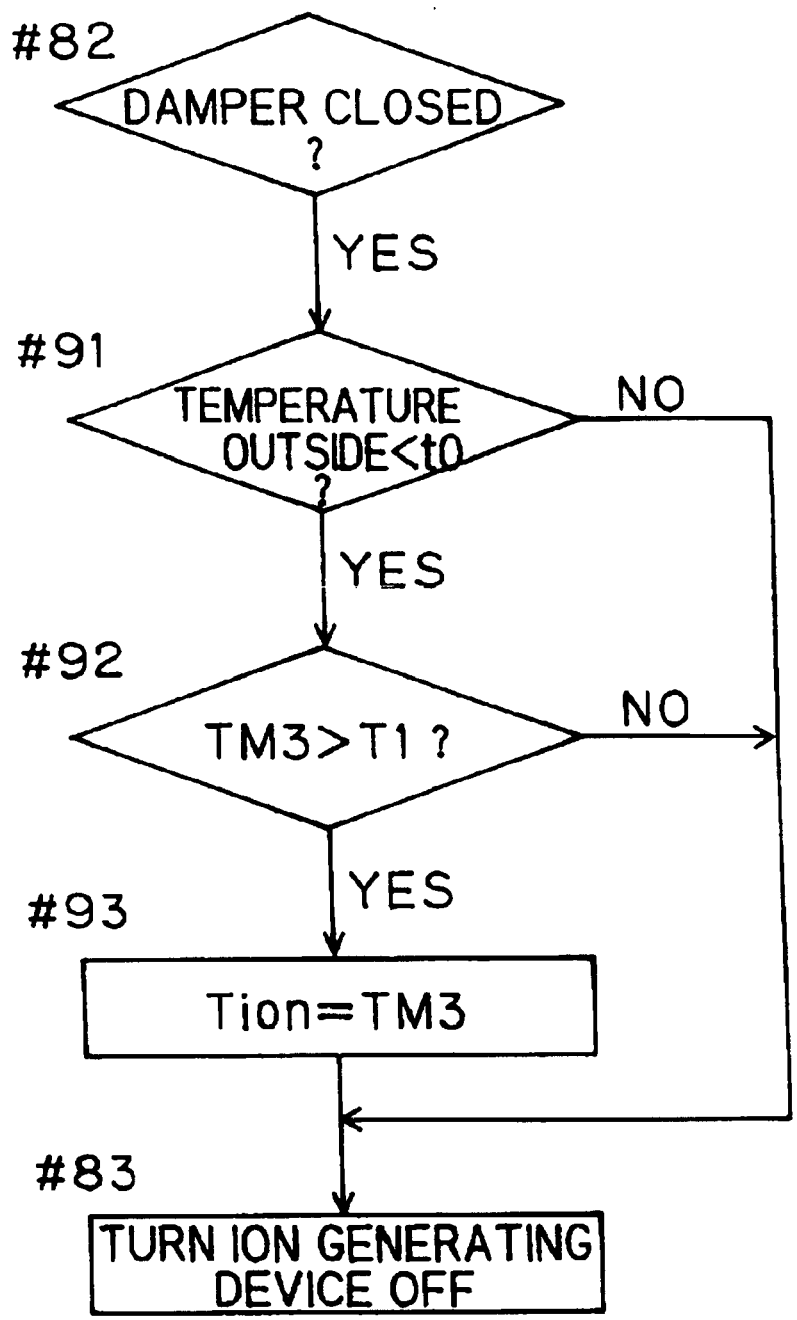
FIG. 12 is a flow chart illustration another example of the operation for condensation prevention of the refrigerator of the first embodiment of the invention.

The ion generating device 11 may be stopped according to the result of detection of the temperature outside. Specifically, when a procedure for exercising control according to the temperature outside as shown in FIG. 12 is inserted between steps #82 and #83 of FIG. 11, even if the set driving period Tion has not been reached, the ion generating device 11 is stopped so as not to generate ions thereafter. This also makes it possible, just as described above, to stop generating more ions than are necessary when the temperature outside is low and thereby minimize the increase in the ozone level so as to achieve adequate sterilization.

In step #91, whether the temperature outside is lower than a predetermined temperature t0 or not is checked. If the temperature outside is equal to or higher than the predetermined temperature t0, the flow proceeds to step #82, where the operation described earlier is performed. If the temperature outside is lower than the predetermined temperature t0, then, in step #92, whether the timer TM3 has counted past a predetermined period T1 (for example, 5 minutes) or not is checked.

If the timer TM3 has not yet counted the predetermined period T1, the flow proceeds to step #83.

If the timer TM3 has counted the predetermined period T1, and a predetermined number of ions have been generated, then the flow proceeds to step #93, where the value of the timer TM3 is substituted in the set driving period Tion of the ion generating device 11. Then, the flow proceeds to step #83.

Since the value of the timer TM3 is equal to the driving period Tion, when the flow returns to the main routine, the condition in step #22 is satisfied and thus, in step #23, the ion generation stopping procedure is performed. As a result, according to the result of detection of the temperature outside, even if the set driving period Tion has not been reached, the ion generating device 11 is stopped so as not to generate ions thereafter. It is also possible to distinguish cases where the opening and closing of the damper 17a is requested as a result of the detection of the temperature inside the refrigerator compartment or the temperature outside from cases where it is requested as a result of a request for the opening and closing of a door or other requests so that, if temperature is involved, resetting is performed even if the ion generation period still remains. This helps further reduce the generation of ozone and achieve adequate sterilization.

In step #28 of the main routine, since the temperatures inside the refrigerator compartment 2 and the freezer compartment 3 have already dropped to the predetermined temperatures, the compressor 46 is stopped. In step #29, to store the on period of the compressor 46, which has thus far been operating, the value of the timer TM2 is substituted in the on period Ton. In step #30, the timer TM2 is restarted to start counting the off period of the compressor 46.

Then, the flow returns to step #12, and repeats steps #12 to #30. If a predetermined long period (for example, 500 hours in this embodiment) has elapsed since the ion generating device 11 was driven last time, it is assumed that the ozone in the refrigerator compartment 2 and the vegetables compartment 4 has dissipated. Therefore, in steps #72 and 73 (see FIG. 10), the timer TM1 is restarted every time the ion generating device 11 is turned off, and, when the timer TM1 becomes equal to 500 hours, this is recognized in step #12, so that the flow proceeds to step #11, where all the variables and timers are initialized.

When the ion generating device is driven for the first time after the full initialization in step #11, the driving period Tion of the ion generating device may be set to be shorter. For example, simultaneously with the full initialization, a flag Ffst is set to "1." When the ion generation starting procedure is performed in step #19, before step #59 of FIG. 9, whether the flag Ffst is "1" or not is checked. If the flag Ffst is "1," the driving period Tion is set to be, for example, 7 minutes, "0" is substituted in the flag Ffst, and the flow proceeds to step #62. If the flag Ffst is "0," the flow proceeds to step #59.

With this flow, when the refrigerator 1 is purchased and is connected to a power outlet for the first time, and then the ion switch is turned on to drive the ion generating device 11, its driving period is short, and therefore only a small amount of ozone is generated. Thus, it is possible to realize a refrigerator that does not make the user smell the ozone odor and that thus does not cause discomfort to the user when the inside of the storage compartments has been cooled and articles to be stored is put therein, even without the masking effect, i.e. the effect of the ozone odor being masked by the smells emanating from food.

In this embodiment, the cool air inside a refrigerator is sterilized by positive and negative ions. This eliminates the need for a collecting electrode or the like for collecting positive ions. Thus, it is possible to alleviate damage to stored articles with a simple structure.

Moreover, corona discharge takes place from an electrode to which substantially no opposed electrode is provided. This prevents absorption, due to a potential difference, of the positive and negative ions generated. As a result, the ions are spread in a wide area in the circulation passage of cool air even without a blow of air. The ions of opposite polarities flock together on the surface of airborne bacteria, and the radicals produced by the ions colliding with one another kill airborne bacteria in a wide area. Thus, it is possible to achieve a higher sterilizing effect without increasing the blowing power and thus without complicating the structure of the device. Moreover, both positive and negative voltages are applied to the electrode. This prevents the electric circuit from being charged, and thus eliminates the need for direct grounding to the earth. This ensures easy installation of a refrigerator in a household.

Moreover, it is also possible to minimize the residual ozone that is generated when discharge takes place and remains thereafter, and thereby prevent discomfort to the user and hazards to his or her health. In this embodiment, positive and negative ions are generated by corona discharge; however, it is possible to achieve the same effect with positive and negative ions generated by any other method.

Figure 13:
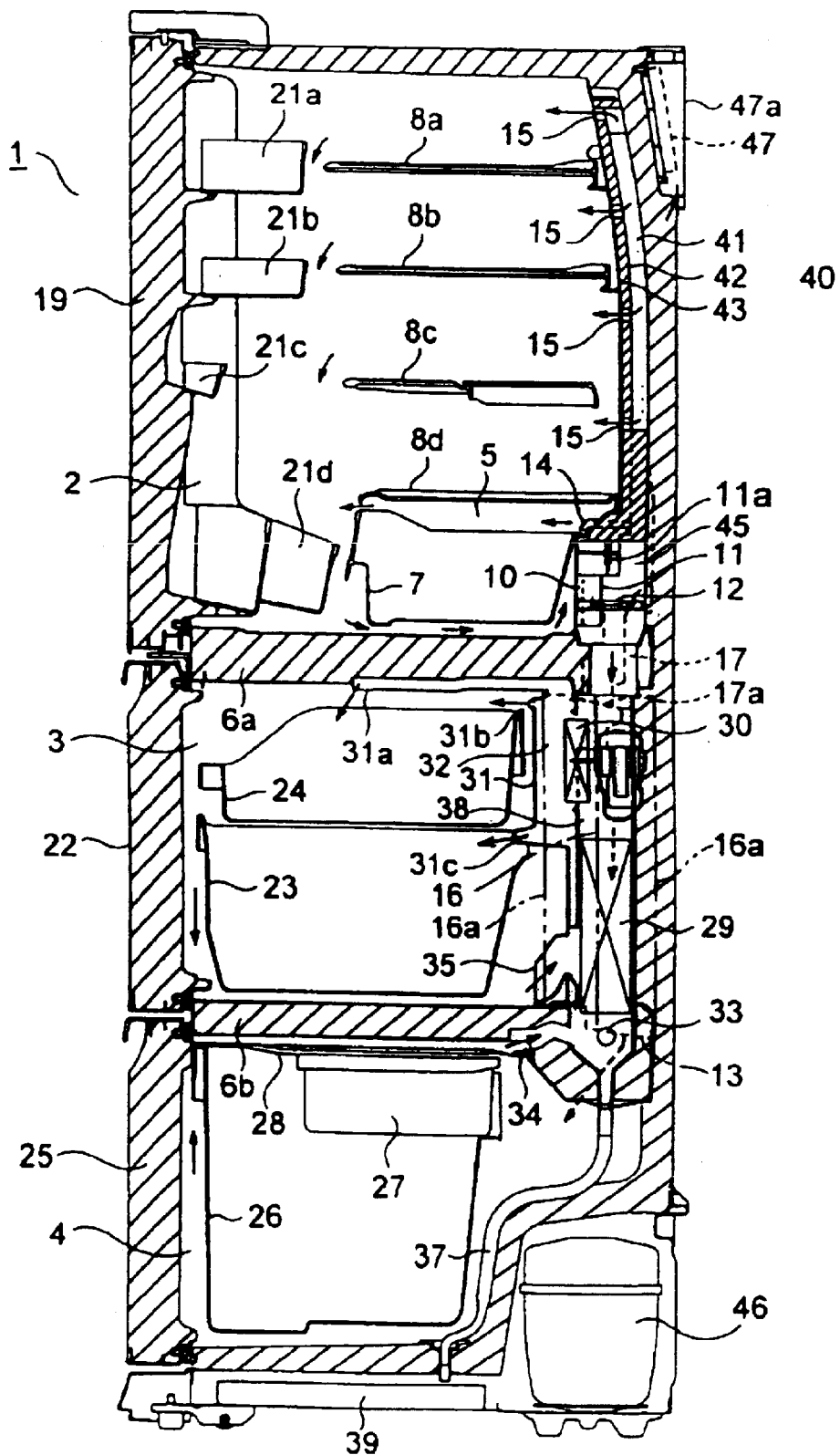
FIG. 13 is a side sectional view of the refrigerator of a second embodiment of the invention.
Figure 14:
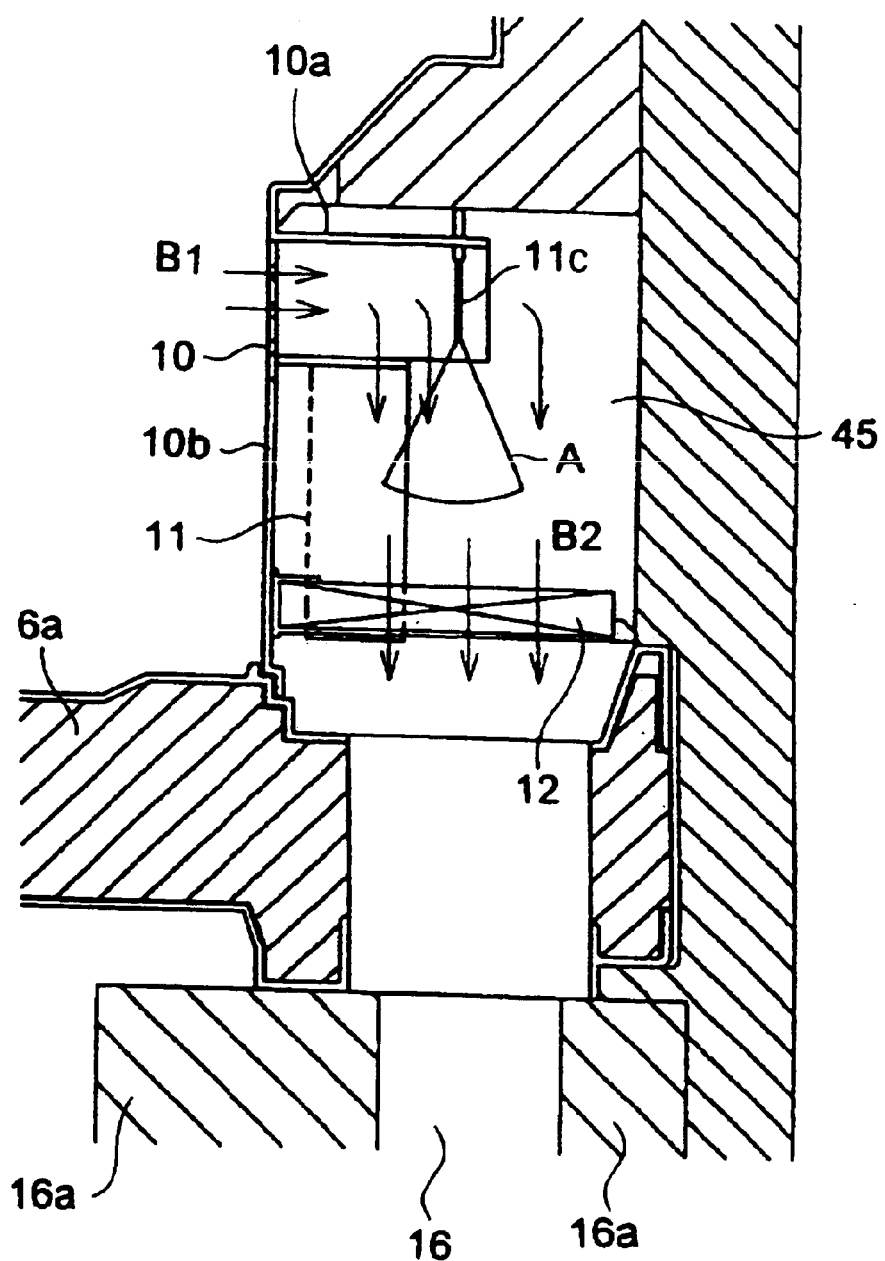
FIG. 14 is a side sectional view of the ion generation chamber of the refrigerator of the second embodiment of the invention.
Figure 15:
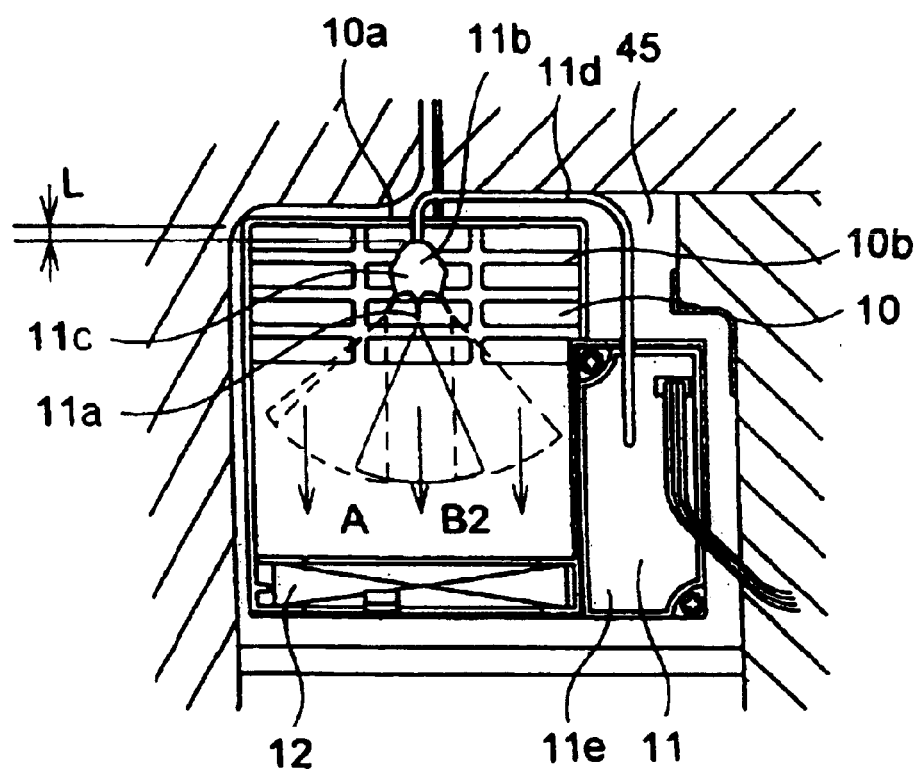
FIG. 15 is a rear view of the ion generation chamber of the refrigerator of the second embodiment of the invention.

FIG. 13 is a side sectional view showing the refrigerator of a second embodiment of the invention. FIGS. 14 and 15 are a side sectional view and a rear view, respectively, of the ion generation chamber of the refrigerator of this embodiment. For convenience' sake, in these figures, such members as are found also in the first embodiment described above and shown in FIGS. 1 to 5 are identified with the same reference numerals.

Here, the only difference from the first embodiment is that the support 10a that supports the electrode portion 11c is formed integrally with an upper portion of the grille 10b, and the needle-like electrode 11a is arranged so as to be suspended from an upper portion of the ion generation chamber 45. In other respects, the structure here is the same as in the first embodiment.

As described earlier, if the distance L between the support 10a and the needle-like electrode 11a is too short, when condensation collects on the support 10a, there is a risk of a high voltage being applied to the support 10a. To avoid this, the distance L is set to be 3.5 mm or longer (for example, 5 mm) so as to place the support 10a sufficiently away from the needle-like electrode 11a to obtain secure insulation.

On the other hand, when the needle-like electrode 11a is arranged close to the support 10a, ions are discharged from a position near the ceiling surface inside the ion generation chamber 45. This permits the ions to keep contact with the cool air for a longer period, and thus helps enhance the sterilization effect, as will be described later. Accordingly, in this embodiment, the distance L is set to be 5 mm to secure a satisfactory sterilization effect and simultaneously permit the high voltage to be applied always stably to the needle-like electrode 11a so that corona discharge takes place securely and ions are discharged stably.

As shown in FIG. 14, the cool air that flows through the cool air return port 10 into the ion generation chamber 45 in the direction indicated by arrows B1 then changes its direction as indicated by arrows B2 and is then introduced into the cool air passage 16. The ions discharged from the needle-like electrode 11a are, as shown in the portion marked "A" in the figure, discharged in high concentrations in a region covering a radiation angle of about 45° with respect to each tip of the needle-like electrode 11a. The needle-like electrode 11a is arranged in such a way that the high ion density region (the portion A) lies along the flow direction (the direction B2) of the cool air.

This alleviates the loss of ions resulting from the discharged ions colliding with a wall surface, and in addition permits the ions to be carried by the cool air easily so that the ions make contact with the cool air in a wide area in the flow direction of the cool air. This helps further enhance the sterilization effect. From the tips of the needle-like electrode 11a, ions are discharged also in low concentrations outside the region covering a radiation angle of about 45°.

Moreover, in a case where, as shown in FIG. 15, the needle-like electrode 11a is so shaped as to have a plurality of pointed tips 11c, by making the individual tips point in different directions, it is possible to discharge ions in the highest concentration in the direction B2 and in satisfactorily high concentrations in as wide a range of angles as possible. Likewise, not only inside the ion generation chamber 45, wherever there is a flow of cold air, by discharging ions along the flow of cold air, it is possible to enhance the sterilizing effect.

Moreover, since the deodorizing device 12 is arranged blow the needle-like electrode 11a (on the downstream side thereof), the ions are discharged uniformly to over the entire top surface of the deodorizing device 12. This makes it possible to securely kill the airborne bacterial caught by the deodorizing device 12 and thereby further enhance the sterilizing effect.

Here, by arranging the deodorizing device 12 close to the ion generating device 11, it is possible to kill in large numbers the airborne bacteria caught by the deodorizing device 12. However, ions are discharged from the needle-like electrode 11a along the flow of cool air, and therefore, by arranging the deodorizing device 12 from the ion generating device 11, it is possible to further enhance the sterilizing effect.

That is, carried by the flow of cool air, the ions reach farther, and thus airborne bacteria are kept in contact with the ions for a long period and are thus killed and reduced before they reach the deodorizing device 12. Then, the deodorizing device 12 catches airborne bacteria and thereby reduces the number of airborne bacteria that manage to pass therethrough. Then, the airborne bacteria caught by the deodorizing device 12 are killed by the ions that reach the deodorizing device 12. By treating the deodorizing device 12 with antibacterial treatment, it is possible to enhance the sterilizing effect.

Since the ions generated by the ion generating device 11 are discharged toward the deodorizing device 12, most of the ions dissipate by killing the airborne bacteria caught by the deodorizing device 12. Thus, the generated ions dissipate inside the ion generation chamber 45, and this prevents deterioration of the inside of the vegetables compartment 4 and the cool air passage 16 due to ions. The wall surfaces of the ion generation chamber 45 may be coated with a coating of metal or of an ion-resistant material that prevents deterioration caused by ions. Alternatively, the wall surfaces of the ion generation chamber 45 may be covered with sheets of metal.

Arranging the deodorizing device 12 on the upstream side of the ion generating device 11 prevents ions from making contact with the low-temperature deodorizing catalyst and the absorbent and thereby losing their ionicity. This helps widen the area in which ions are present and thereby enhance the sterilizing effect. In this way, the deodorizing device 12 may be arranged to suit the purpose of providing it.

Figure 16:
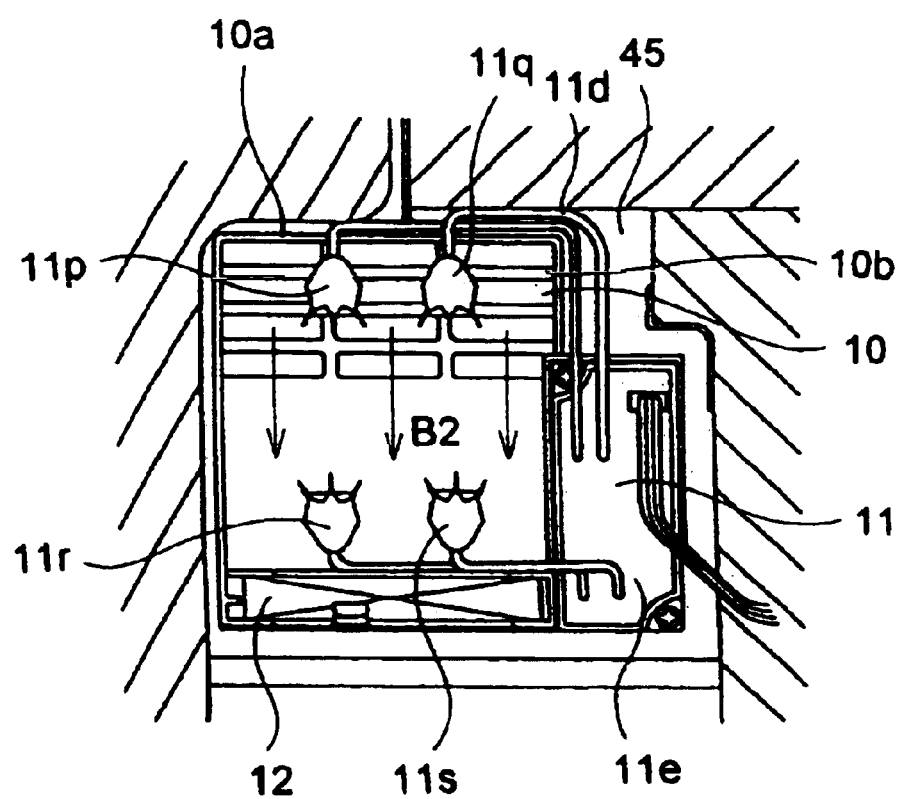
FIG. 16 is a rear view of the ion generation chamber of the refrigerator of a third embodiment of the invention.

FIG. 16 is a rear view showing the ion generation chamber of the refrigerator of a third embodiment of the invention. For convenience' sake, such members as are found also in the second embodiment described above and shown in FIGS. 13 to 15 are identified with the same reference numerals. In this embodiment, the ion generating device 11 is provided with four needle-like electrodes 11p, 11q, 11r, and 11s, to which voltages controlled by the power supply 11e are applied individually. In other respects, the structure here is the same as in the second embodiment.

The needle-like electrodes 11p and 11q are, as in the second embodiment, arranged so as to be suspended from an upper portion of the ion generation chamber 45. The needle-like electrodes 11r and 11s are arranged in such a way that ions are discharged upward from a lower portion of the ion generation chamber 45. The needle-like electrodes 11p and 11s generate positive ions, and the needle-like electrodes 11q and 11r generate negative ions.

The needle-like electrodes 11p and 11q discharge ions along the flow of cool air flowing in the direction indicated by arrows B2, and thus, as in the second embodiments, airborne bacteria floating in the cool air are kept in contact with the ions for a long period and are thereby killed. On the other hand, the needle-like electrodes 11r and 11s discharge ions against the flow of cool air flowing in the direction indicated by arrows B2. Thus, the ions collide with the cool air and are thereby spread throughout the ion generation chamber 45. This permits ions to be distributed in a wider area, and thus helps further enhance the sterilizing effect.

If positive and negative ions are generated with a single needle-like electrode 11a (see FIG. 14), when ions start being generated, part of them cancel each other and thereby reduce the effective number of ions generated. In this embodiment, positive ions are generated with one group of electrodes (11p and 11s) and negative ions are generated with another group of electrodes (11q and 11r). This helps increase the effective number of ions generated.

In addition, the numbers of positive and negative ions generated can be varied easily. Moreover, the electrodes from which positive ions are generated and the electrodes from which negative ions are generated are arranged so as to be adjacent to each other. This permits positive and negative ions to be mixed and distributed uniformly and thereby facilitates them to flock together, ensuring a satisfactory sterilizing effect.

Furthermore, by arranging the adjacent electrodes at least 10 mm (for example, 30 mm) apart from each other, it is possible to use ions effectively for sterilization with almost no cancellation between the positive and negative ions generated from the individual electrodes. Moreover, by stopping the application of voltages to the needle-like electrodes 11q and 11r while voltages are applied to the needle-like electrodes 11p and 11s and by stopping the application of voltages to the needle-like electrodes 11p and 11s while voltages are applied to the needle-like electrodes 11q and 11r, it is possible to further reduce cancellation between positive and negative ions.

In addition, for example, by applying voltages to the needle-like electrodes 11q and 11p alternately or simultaneously and stopping the application of voltages to the needle-like electrodes 11r and 11s for a predetermined period, it is possible to vary easily the number of ions generated.

The needle-like electrodes 11p, 11q, 11r, and 11s may be used to generate ions of one polarity each, or alternatively they may be used to generate both positive and negative ions in a different ratio each. For example, the needle-like electrodes 11p and 11s are used to generate more positive ions and the needle-like electrodes 11q and 11r are used to generate more negative ions.

Even in this case, the electrodes that mainly generate positive ions are distinguished from the electrodes that mainly generate negative ions, and thus it is possible to reduce cancellation between ions and thereby increase the effective number of ions generated. Here, by differentiating the circuit configuration, applied voltage, electrode shape, electrode material, and the like, it is possible to vary easily the balance of ions generated.

In the second and third embodiments, it is possible to achieve the same effect as in the first embodiment. Moreover, it is possible to reduce the loss of ions resulting from the discharged ions colliding with a wall surface, and to permit the ions to be carried by cool air easily so that the ions make contact with the cool air in a wide area in the flow direction of the cool air. This helps enhance the sterilization effect.

In the second and third embodiments, there is no need to use a needle-like electrode. For example, if ions are generated by applying a voltage between electrodes that are so arranged as to be opposed to each other with an insulator in between, those opposed electrodes make the device as a whole larger, but ions are generated along the flow of cool air, which enhances the sterilizing effect. Moreover, sterilization may be achieved by the use of a sterilizing substance other than ions. Examples of sterilizing substances include tangible agents such as chemicals and intangible agents such as heat and ultraviolet rays, though these are not physically substances.

Figure 17:
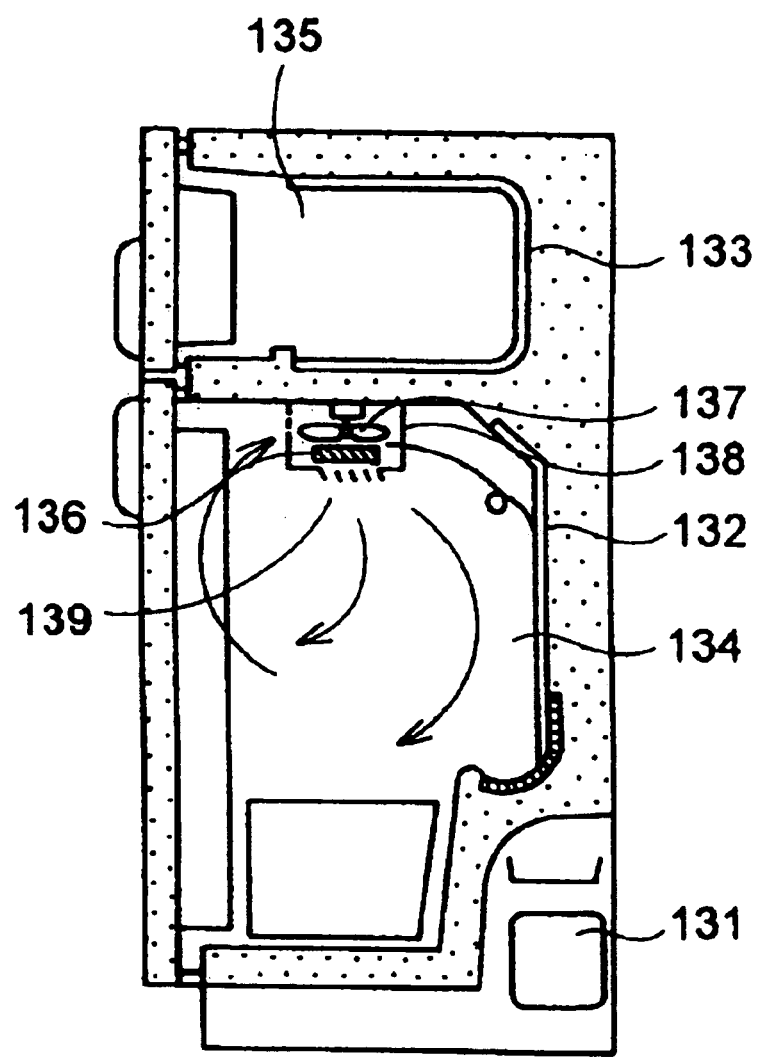
FIG. 17 is a side sectional view of the refrigerator of a fourth embodiment of the invention.

FIG. 17 is a side sectional view showing the direct-cooling-type refrigerator of a fourth embodiment of the invention. In this figure, reference numeral 131 represents a compressor, reference numeral 132 represents a refrigerator compartment chiller arranged in a refrigerator compartment 134, and reference numeral 133 represents a freezer compartment chiller arranged in a freezer compartment 135. Reference numeral 136 represents an ion generating device similar to those of the first to third embodiments. This ion generating device 136 is housed in a case 138 arranged in an upper portion of the refrigerator compartment 134. Reference numeral 137 represents a fan. As the fan 137 rotates, positive and negative ions are discharged into the refrigerator compartment 134 through an outlet port 139 formed in the case 138. In this way, as in the first to third embodiments, airborne bacteria floating in the refrigerator compartment 134 are deactivated to alleviate damage to food stored therein.

Figure 18:
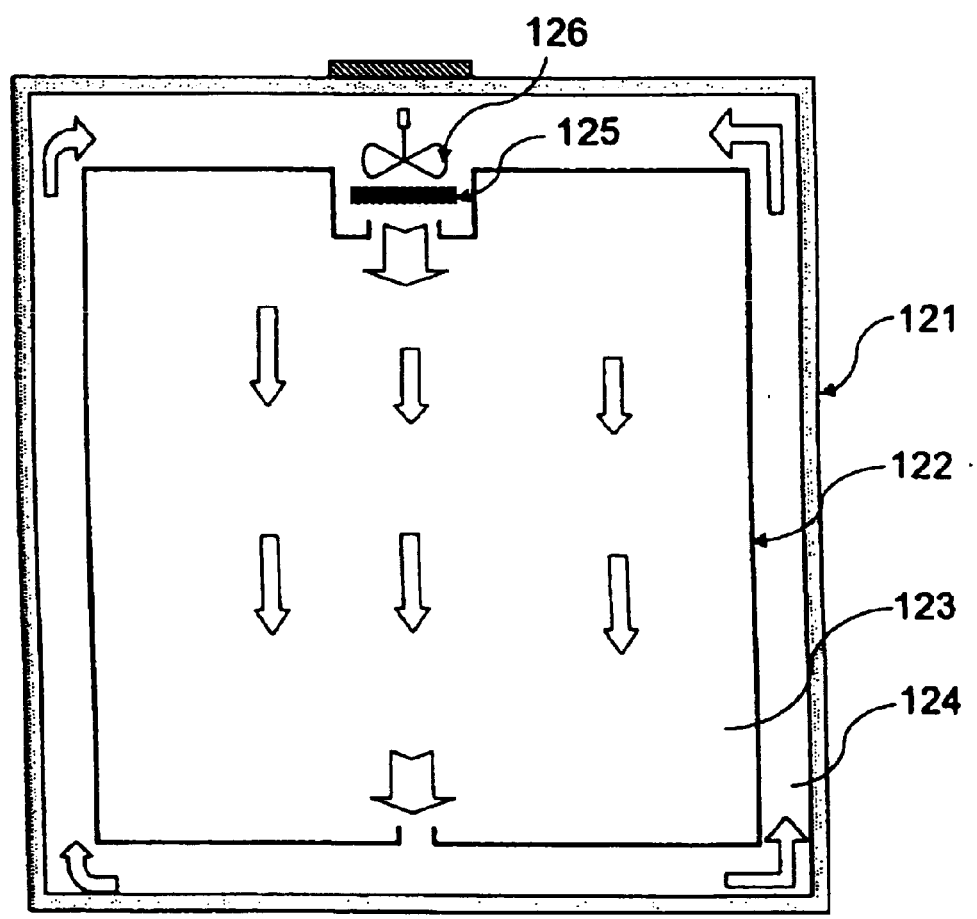
FIG. 18 is a side sectional view of the food storeroom of a fifth embodiment of the invention.

FIG. 18 is a sectional view, as seen from the top, showing the food storeroom 121 of a fifth embodiment of the invention. The food storeroom 121 is so designed that its top face is opened and closed to store food therein. In this figure, reference numeral 122 represents partitions that are arranged predetermined distances away from the four side walls of the food storeroom 121. These partitions 122 divide the inside of the food storeroom 121 into a food placement portion 123 and a cool air circulation passage 124. Reference numeral 125 represents an ion generating device similar to those of the first to third embodiments. Reference numeral 126 represents a fan. As the fan 126 rotates, positive and negative ions are discharged into the food storeroom 121. The fan 126 makes air inside the food storeroom 121 flow as indicated by arrows in the figure, and the positive and negative ions are carried by this flow of air and are thereby circulated. In this way, as in the first to third embodiments, airborne bacteria floating in the air are deactivated to alleviate damage to the food.

Figure 19:
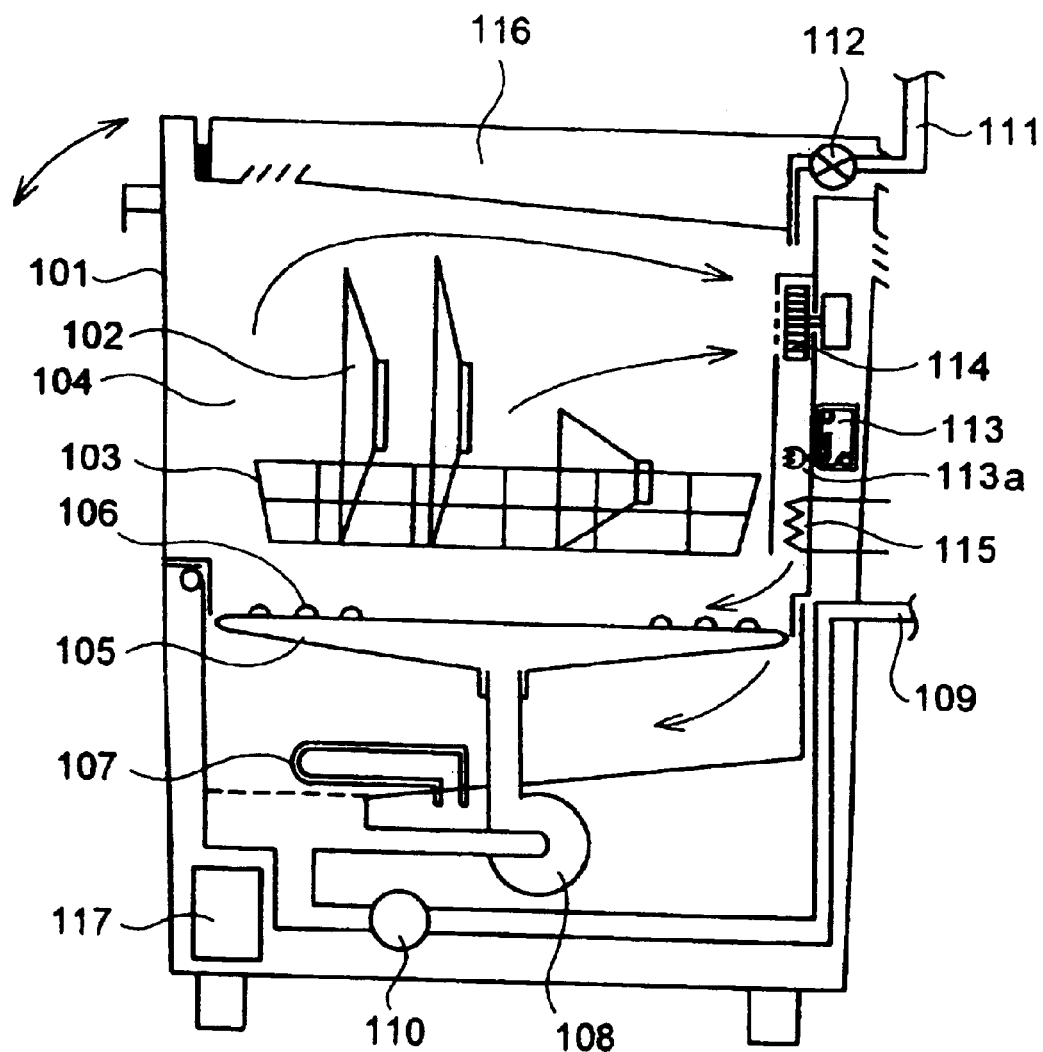
FIG. 19 is a side sectional view of the dish washer/dryer of a sixth embodiment of the invention.

FIG. 19 is a sectional view schematically showing the dish washer/dryer of a sixth embodiment of the invention. The dish washer/dryer of this embodiment is provided with an ion generating device 113 similar to those of the first to third embodiments, and an electrode portion 113a of the ion generating device 113 is arranged in a circulation passage through which hot air is circulated inside a dish storage compartment 104 in a drying process. During or after the drying process, positive and negative ions are discharged from the electrode portion 113a and are circulated inside the dish storage compartment 104. This achieves deodorizing and the killing of airborne bacteria inside the dish storage compartment 104.

In the front face of the dish storage compartment 104, a front door 101 is provided that is opened and closed when tableware or the like is put in and taken out. Inside the dish storage compartment 104, a rack 103 is arranged in which to put tableware 102, and, below the rack 103, a rotary washing nozzle 105 is arranged so as to protrude toward a substantially central portion of the dish storage compartment 104. The washing nozzle 105 has a plurality of jet holes 106 formed therein, through which it discharges a jet of washing water supplied from a washing pump 108. Below the washing nozzle 105 is provided a heater 107 for heating the washing water.

In a lower portion of the dish storage compartment 104 is arranged a drain pump 110 for discharging the washing water into a drain pipe 109. In an upper portion of the dish storage compartment 104, a supply pipe 111 is arranged through which washing water is fed in. On the way along the supply pipe 111 is arranged a supply valve 112. Moreover, a heat exchange duct 116 is arranged so as to cover the top face of the dish storage compartment 104. The heat exchange duct 116 serves to discharge hot air out of the body of the dish washer/dryer, and to condense steam to return water to the dish storage compartment 104.

In a rear portion of the dish storage compartment 104 are arranged an ion generating device 113, a fan 114, and a heater 115. The fan 114 circulates air to dry the washed tableware 102. Here, hot air heated by the heater 115 is discharged into the dish storage compartment 104. Moreover, the fan 114 also circulates the positive and negative ions discharged from the electrode portion 113a of the ion generating device 113 inside the dish storage compartment 104. Reference numeral 117 represents a controller for controlling the entire dish washer/dryer.

How this dish washer/dryer operates will be described. First, the front door 101 is opened, and articles of tableware 102, utensils, and the like to be washed are put in predetermined positions in the rack 103. Then, the rack 103 is put in the dish storage compartment 104, and then, with special detergent thrown in, the dish washer/dryer starts being operated.

Then, the supply valve 112 is opened so that a predetermined amount of washing water is supplied through the supply pipe 111 to the dish storage compartment 104. Then, the washing pump 108 is operated so that pressurized washing water is, together with the detergent, jetted through the jet holes 106 of the washing nozzle 105 to the tableware 102 to achieve washing.

Thereafter, a rinsing process and a drying process are performed. After completion of the drying process, the fan 114 and the ion generating device 113 are driven for a predetermined period (about 30 minutes) so that the positive and negative ions discharged from the electrode portion 113a are discharged into the dish storage compartment 104 and are circulated as indicated by arrows in the figure. The generation of ions may be started halfway in the drying process to shorten the overall operation time. This is possible because, even if water drops collect on the electrode portion 113a, they will be vaporized and dried by hot air.

In this embodiment, by discharging positive and negative ions into the dish storage compartment 104 and circulating them inside it, it is possible, as in the first to fifth embodiments, to achieve deodorizing and the killing of airborne bacteria inside the dish storage compartment 104. This makes hygienic storage of tableware, utensils, and the like possible.

Figure 20:
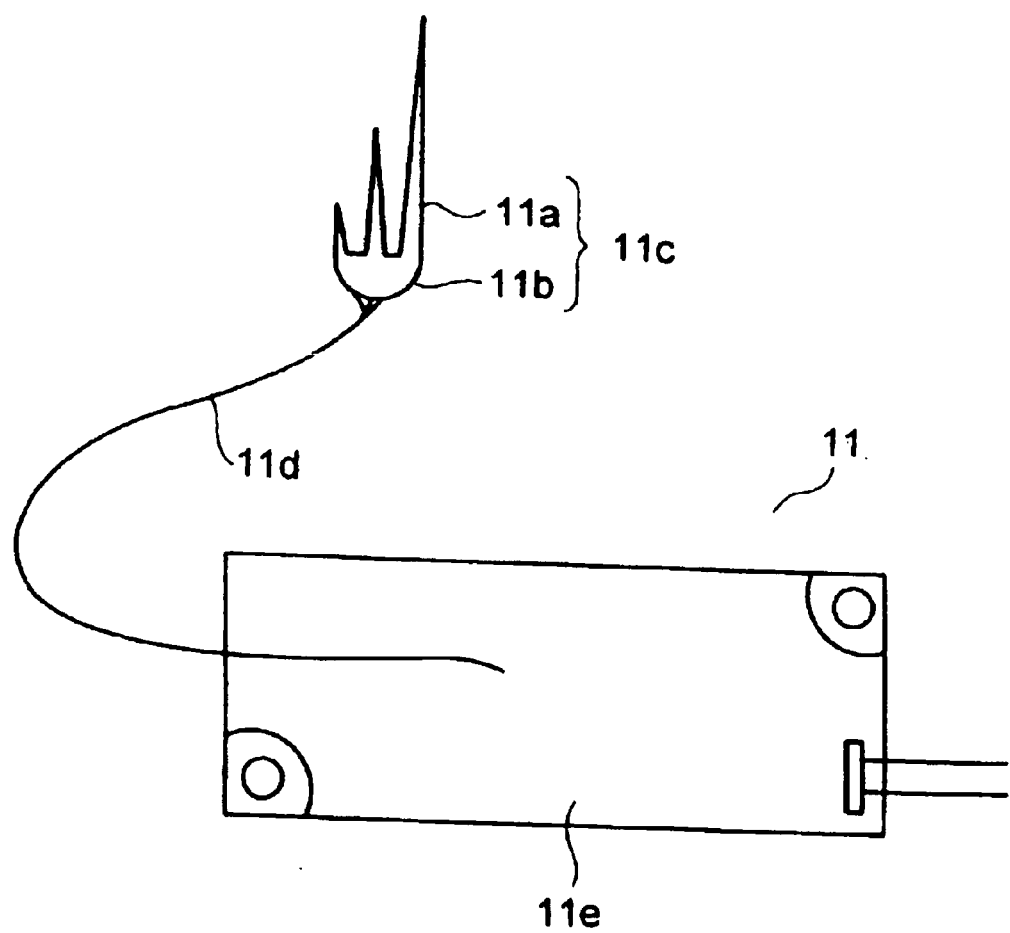
FIG. 20 is a diagram schematically showing another example of the shape of the electrode portion of the ion generating device incorporated in the first to sixth embodiments of the invention.
Figure 21:
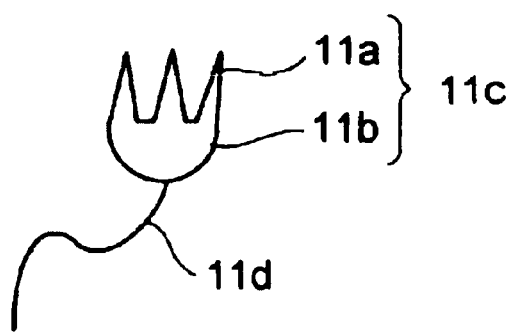
FIG. 21 is a diagram schematically showing another example of the shape of the electrode portion of the ion generating device incorporated in the first to sixth embodiments of the invention.
Figure 22:
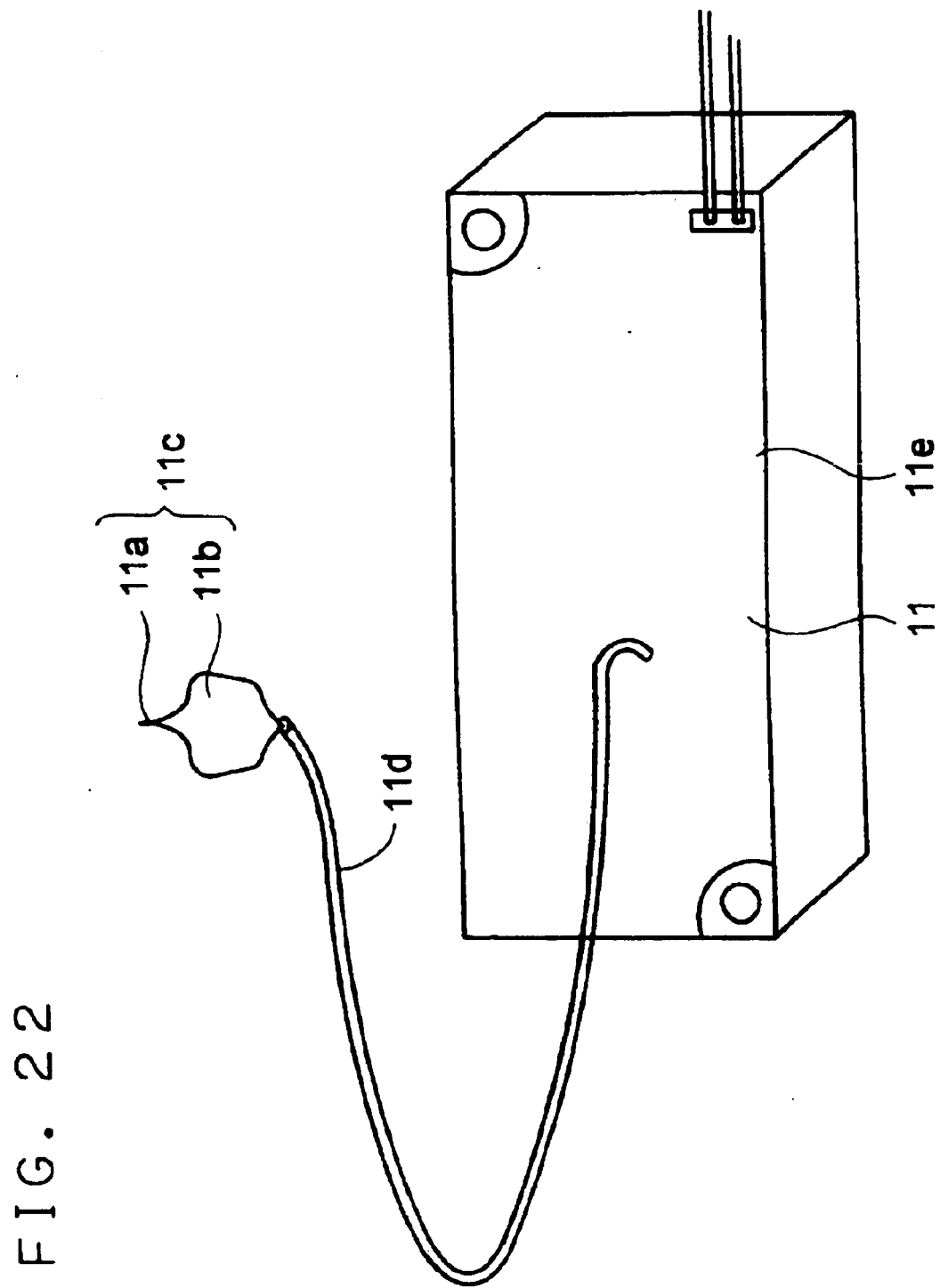
FIG. 22 is a diagram schematically showing another example of the shape of the electrode portion of the ion generating device incorporated in the first to sixth embodiments of the invention.

In the first to sixth embodiments, the electrode portion of the ion generating device may have any other shape than specifically shown in FIG. 4 described earlier. FIGS. 20 to 22 show other examples of the shape of the electrode portion 11c, where, for convenience' sake, such members as are found also in FIG. 4 are identified with the same reference numerals.

In the electrode portion 11c shown in FIG. 20, the plurality of pointed tips of the needle-like electrode 11a formed so as to protrude from the flat portion 11b have different lengths. In the electrode portion 11c shown in FIG. 21, the plurality of pointed tips of the needle-like electrode 11a formed so as to protrude from the flat portion 11b point in the same direction. In the electrode portion 11c shown in FIG. 22, the needle-like electrode 11a formed so as to protrude from the flat portion 11b has a single pointed tip. With any of these shapes, it is possible to achieve the same effect as in the first to sixth embodiment.

Figure 23:
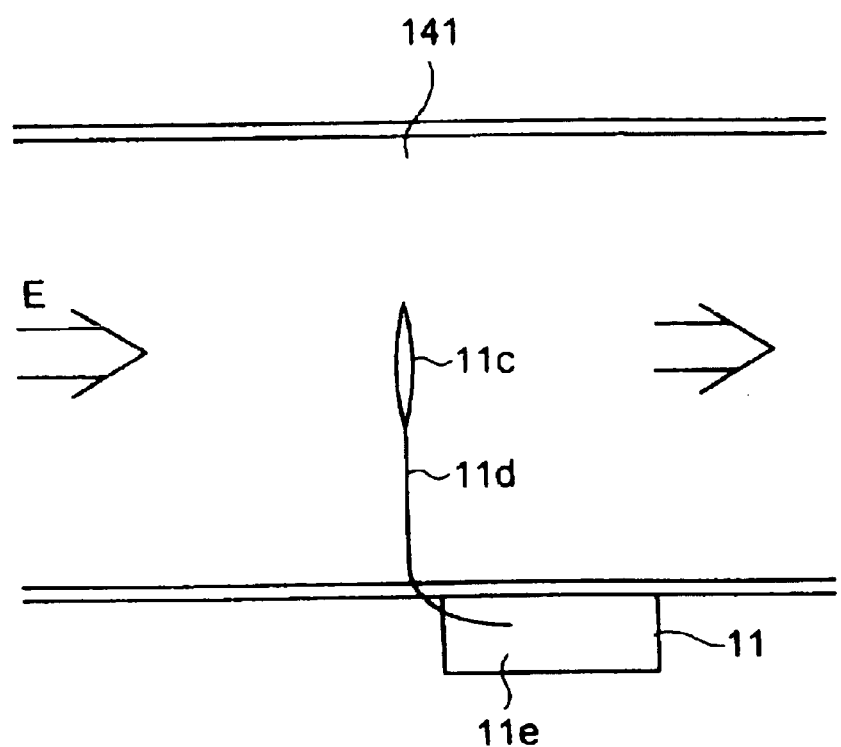
FIG. 23 is a diagram schematically showing another example of the arrangement of the electrode portion of the ion generating device incorporated in the first to sixth embodiments of the invention.

The electrode portion 11c may be arranged otherwise than parallel to the flow direction of air. For example, as shown in FIG. 23, the electrode portion 11c may be arranged perpendicularly to the flow of air E circulating through the air circulation passage 141.

The first to sixth embodiments described above deal with refrigerators, a food storeroom, and a dish washer/dryer. However, an ion generating device similar to those described above may be incorporated in any other type of storeroom. That is, the same effect as described above is achieved in any type of storeroom consisting of a space having predetermined dimensions and separated from the space surrounding it for the purpose of storing articles therein, for example, freezers, cupboards, dish dryers, dish washers, warming/heating cabinets in which articles are stored at temperatures higher than room temperature, storehouses for provisions, and lockers. Depending on its type, a storeroom may have its storage space divided into a plurality of storage compartments.

A refrigerator may be a storehouse furnished with a cooling function, and a freezer may be a storehouse furnished with a freezing function. That is, what the present invention calls storerooms include anything in which articles are stored in a cooled state, such as storerooms mounted on refrigerator trucks and showcases of which the inside is kept cool.

Industrial Applicability

As described above, according to the present invention, the air inside a storage compartment of a refrigerator or the like is sterilized with positive and negative ions. Thus, it is possible to alleviate damage to stored articles with a simple structure without the need for a collecting electrode or the like for collecting positive ions.

Moreover, corona discharge takes place from an electrode to which substantially no opposed electrode is provided. This prevents absorption, due to a potential difference, of the positive and negative ions generated. As a result, the ions are spread in a wide area in the circulation passage of cool air even without a blow of air. The ions of opposite polarities flock together on the surface of airborne bacteria, and the radicals produced by the ions colliding with one another kill airborne bacteria in a wide area.

Thus, it is possible to achieve a higher sterilizing effect without increasing the blowing power and thus without complicating the structure of the device. Moreover, both positive and negative voltages are applied to the electrode. This prevents the electric circuit from being charged, and thus eliminates the need for direct grounding to the earth. This ensures easy installation of a refrigerator in a household. Moreover, it is also possible to minimize the residual ozone that is generated when discharge takes place and remains thereafter, and thereby prevent discomfort to the user and hazards to his or her health.

Furthermore, by discharging a sterilizing substance such as ions along the flow of cool air, it is possible to reduce the loss of ions resulting from the discharged ions colliding with a wall surface, and to permit the ions to be carried by the cool air easily so that the ions make contact with the cool air in a wide area in the flow direction of the cool air. This helps further enhance the sterilization effect.

What is claimed is:

1. A storeroom comprising an electrode to which a high voltage is applied to generate positive and negative ions, wherein the positive and negative ions are discharged from the electrode together into an air flow passage through which air is circulated in order to kill airborne germs floating in the air.

2. A storeroom comprising an electrode to which no opposed electrode is provided and to which a high voltage is applied to generate positive and negative ions, wherein the positive and negative ions are discharged together into an air flow passage through which air is circulated in order, to kill airborne germs floating in the air.

3. A storeroom comprising an ion generating device that does not require grounding, wherein a high voltage is applied to an electrode of the ion generating device to generate positive and negative ions, and the positive and negative ions are discharged together into an air flow passage through which air is circulated in order to kill airborne germs floating in the air.

4. A storeroom comprising an ion generating device having no grounded electrode, wherein a high voltage is applied to an electrode of the ion generating device to generate positive and negative ions, and the positive and negative ions are discharged together into an air flow passage through which air is circulated in order to kill airborne germs floating in the air.

5. A storeroom comprising an electrode to which a high voltage is applied to generate $H^+(H_2O)_n$ as positive ions and $O_2^-(H_2O)_m$ as negative ions, wherein the positive ions $H^+(H_2O)_n$ and the negative ions $O_2^-(H_2O)_m$ are discharged from the electrode into an air flow passage through which air is circulated in order to kill airborne germs floating in the air.

6. A storeroom comprising an electrode to which no opposed electrode is provided and to which a high voltage is applied to generate $H^+(H_2O)_n$ as positive ions and $O_2^-(H_2O)_m$ as negative ions, wherein the positive ions $H^+(H_2O)_n$ and the negative ions $O_2^-(H_2O)_m$ are discharged into an air flow passage through which air is circulated in order to kill airborne germs floating in the air.

7. A storeroom comprising an ion generating device that does not require grounding, wherein a high voltage is applied to an electrode of the ion generating device to generate $H^+(H_2O)_n$ as positive ions and $O_2^-(H_2O)_m$ as negative ions, and the positive ions $H^+(H_2O)_n$ and the negative ions $O_2^-(H_2O)_m$ are discharged into an air flow passage through which air is circulated in order to kill airborne germs floating in the air.

8. A storeroom comprising an ion generating device having no grounded electrode, wherein a high voltage is applied to an electrode of the ion generating device to generate $H^+(H_2O)_n$ as positive ions and $O_2^-(H_2O)_m$ as negative ions, and the positive and negative ions are discharged into an air flow passage through which air is circulated in order to kill airborne germs floating in the air.

9. A storeroom as claimed in claim 1, wherein one or more storage compartments are provided and the air flow passage includes at least one of the storage compartments so that the positive and negative ions are discharged into said at least one of the storage compartments.

10. A storeroom as claimed in claim 1, wherein radicals produced from the positive and negative ions kill airborne bacteria floating inside the air flow passage.

11. A storeroom as claimed in claim 1, wherein one or more storage compartments are provided, at least one of the storage compartments is fitted with a duct through which air is introduced thereto, and the electrode is arranged in the duct.

12. A storeroom as claimed in claim 1, wherein at least one storage compartment is provided, and controlling means for controlling generation of the ions in synchronism with circulation of air to said at least one storage compartment is provided.

13. A storeroom as claimed in claim 1, wherein at least one storage compartment is provided, cooling means for cooling an inside of said at least one storage compartment is provided, and controlling means for controlling generation of the ions in synchronism with cooling of said at least one storage compartment is provided.

14. A storeroom as claimed in one of claim 1, wherein at least one storage compartment is provided, temperature detecting means is provided in said at least one storage compartment, and controlling means for controlling generation of the ions according to a result of temperature detection by the temperature detecting means is provided.

15. A storeroom as claimed in claim 1, wherein controlling means for controlling generation of the ions according to a result of detection of whether a damper for controlling a flow of air is open or closed is provided.

16. A storeroom as claimed in claim 1, wherein at least one storage compartment is provided, cooling means for cooling an inside of said at least one storage compartment is provided, and controlling means for controlling generation of the ions in synchronism with driving of a compressor constituting part of the cooling means is provided.

17. A storeroom as claimed in claim 1, wherein at least one storage compartment is provided, and controlling means for controlling generation of the ions in synchronism with opening of at least one door for opening and closing said at least one storage compartment or according to a result of detection of opening movement of said at least one door is provided.

18. A storeroom as claimed in claim 1, wherein controlling means for controlling generation of the ions according to temperature outside is provided.

19. A storeroom as claimed in claim 1, wherein at least one storage compartment is provided, cooling means for cooling an inside of said at least one storage compartment is provided, temperature detecting means for detecting temperature inside said at least one storage compartment cooled by the cooling means is provided, and, when the temperature detected by the temperature detecting means becomes higher than a predetermined temperature, in synchronism with cooling of the storage compartment, a voltage is applied to the ion generating device to generate the positive and negative ions.

* * * * *